`US011987805B2`

(12) United States Patent
Jacobs, Jr. et al.

(10) Patent No.: US 11,987,805 B2
(45) Date of Patent: May 21, 2024

(54) ATTB CELL LINE, TRANSGENIC CELL LINES DERIVED THEREFROM, AND METHODS OF MAKING THE SAME

(71) Applicant: Albert Einstein College of Medicine, Bronx, NY (US)

(72) Inventors: William R. Jacobs, Jr., Bronx, NY (US); Lawrence Leung, Flushing, NY (US); Regy Lukose, Flanders, NJ (US); Anna Paula de Oliveira, Bronx, NY (US)

(73) Assignee: ALBERT EINSTEIN COLLEGE OF MEDICINE, Bronx, NY (US)

( * ) Notice: Subject to any disclaimer, the term of this patent is extended or adjusted under 35 U.S.C. 154(b) by 197 days.

(21) Appl. No.: 17/484,476

(22) Filed: Sep. 24, 2021

(65) Prior Publication Data
US 2022/0090146 A1  Mar. 24, 2022

Related U.S. Application Data

(60) Provisional application No. 63/082,701, filed on Sep. 24, 2020.

(51) Int. Cl.
| | |
|---|---|
| C12N 15/01 | (2006.01) |
| C07K 14/35 | (2006.01) |
| C12N 7/00 | (2006.01) |
| C12N 9/22 | (2006.01) |
| C12N 15/09 | (2006.01) |
| C12N 15/11 | (2006.01) |
| C12N 15/90 | (2006.01) |
| C12Q 1/70 | (2006.01) |

(52) U.S. Cl.
CPC ............ *C12N 15/907* (2013.01); *C07K 14/35* (2013.01); *C12N 7/00* (2013.01); *C12N 9/22* (2013.01); *C12N 15/11* (2013.01); *C12Q 1/70* (2013.01); *C12N 2310/20* (2017.05); *C12N 2710/16652* (2013.01); *C12N 2800/80* (2013.01)

(58) Field of Classification Search
None
See application file for complete search history.

(56) References Cited

U.S. PATENT DOCUMENTS

2016/0340661 A1* 11/2016 Cong .................. C12N 15/102

FOREIGN PATENT DOCUMENTS

| WO | 2015089462 A1 | 6/2015 |
| WO | 2015134368 A2 | 9/2015 |
| WO | 2017112868 A1 | 6/2017 |

OTHER PUBLICATIONS

Voutev et al. Bxb1 phage recombinase assists genome engineering in *Drosophila melanogaster*. Bio Techniques 62:37-38 (Jan. 2017).*
International Search Report dated Jan. 21, 2022; International Application No. PCT/US2021/051947; International Filing Date Sep. 24, 2021 (9 pgs).
Loew, et al., "A new PG13-based packaging cell line for stable production of clinical-grade self-inactivating γ-retroviral vectors using targeted integration" Gene Therapy (2010) 17, 272-280.
Matreyek, et al., "An improved platform for functional assessment of large protein libraries in mammalian cells" Nucleic Acids Research, 2020, vol. 48, No. 1 (12 pgs).
Stabell, et al., "Isolation of a cell line for rapid and sensitive histochemical assay for the detection of herpes simplex virus" Journal of Virological Methods, 38 (1992) 195-204.
Written Opinion dated Jan. 21, 2022; International Application No. PCT/US2021/051947; International Filing Date Sep. 24, 2021 (14 pgs).
Barletta, et al., "Identification of expression signals of the mycobacteriophages Bxb1, L1 and TM4 using the *Escherichia-Mycobacterium* shuttle plasmids pYUB75 and pYUB76 designed to create translational fusions to the lacZ gene" Journal of General Microbiology (1992), 138, 23-30.
Xu, et al., "Accuracy and efficiency define Bxb1 integrase as the best of fifteen candidate serine recombinases for the integretion of DNA into the human genome", BMC Biotechnology, 2013, 13:87 (17 pgs).
Cheshenko, et al., "HSV activates Akt to trigger calcium release and promote viral entry: novel canditae target for treatment and suppression" The FASEB Journal, 2013, 27(7): 2584-2599.
Ghosh, et al., "The Orientation of Mycobacteriophage Bxb1 Integration Is Solely Dependent on the Central Dinucleotide of attP and attB", Molecular Cell, vol. 12, pp. 1101-1111, Nov. 2003.
Huang, et al., "Successive and Targeted DNA Integrations in the *Drosophila* Genome by BxB1 and ?C31 Integrases" Genetics, vol. 189, pp. 391-395, Sep. 2011.
Johnson, et al., "Herpes Simplex Viruses Lacking Glycoprotein D Are Unable To Inhibit Virus Penetration: Quantitative Evidence for Virus-Specific Cell Surface Receptors", Journal of Virology, 1988, vol. 62, No. 12, pp. 4605-6412.
Ligas, et al., "A Herpes Simples Virus Mutant in Which Glycoprotein D Sequences Are Replaced by β-Galactosidase Sequences Binds to but is Unable To Penetrate into Cells", Journal of Virology, May 1988, vol. 62, No. 5, pp. 1486-1494.
Mali, et al., "RNA-Guided Human Genome Engineering via Cas9", Science, 2013, 339(6121): 823-826. doi:10.1126/science.1232033.
Matreyek, et al., "A platform for functional assessment of large variant libraries in mammalian cells" Nucleic Acids Research, 2017, vol. 45, No. 11, e102 (12 pgs).

(Continued)

*Primary Examiner* — Nianxiang Zou
(74) *Attorney, Agent, or Firm* — CANTOR COLBURN LLP

(57) ABSTRACT

A genetically modified mammalian cell and genetically modified mammalian cell line comprise a recombination sequence inserted in a target locus on a chromosome of the mammalian cell genome, wherein the recombination sequence comprises Bxb1attB sequence from *Mycobacterium smegmatis*. A transgenic mammalian cell and transgenic mammalian cell line comprise a heterologous nucleic acid stably integrated in a target locus on a chromosome of the mammalian genome, wherein the heterologous nucleic comprises a heterologous gene configured for expression by the transgenic mammalian cell.

44 Claims, 9 Drawing Sheets

Specification includes a Sequence Listing.

(56) References Cited

OTHER PUBLICATIONS

Mediavilla, et al., "Genome organization and characterization of mycobacteriophage Bxb1", Molecular Microbiology (2000) 38(5), 955-970.

Nkrumah, et al., "Efficient site-specific integration in Plasmodium falciparum chromosomes mediated by mycobacteriophage Bxb1 integrase" Nat Methods, 2006, 3(8): 615-621; doi:10.1038/nmeth904.

Ojha, et al., "GroEL1: A Dedicated Chaperone Involved in Mycolic Acid Biosynthesis during Biofilm Formation in *Mycobacteria*", Cell 123, 861-873, Dec. 2, 2005.

Petro, et al., "Herpes simplex type 2 virus deleted in glycoprotein D protects against vaginal, skin and neural disease" Elife, 2015, 4:e06054 (18 pages).

Petro, et al., "HSV-2 ΔgD elicits FcγR-effector antibodies that protect against clinical isolates" JCI Insight Aug. 4, 2016; 1 (12): e88529.

Russell, et al., "Phage Bxb1 integrase mediates highly efficient site-specific recombination in mammalian cells" BioTechniques, vol. 40, No. 4, pp. 460-464 (Apr. 2006).

Thomson, et al., "The Bxb1 recombination system demonstrates heritable transmission of site-specific excision in *Arabidopsis*" BMC Biotechnology, 2012, 12:9, 11 pgs.

Voutev, et al., "Bxb1 phage recombinase assists genome engineering in *Drosophila melanogaster*", BioTechniques vol. 62, No. 1, pp. 37-38 (Jan. 2017) doi 10.2144/000114494.

* cited by examiner

Path to HSV-2:Δ$_g$D1 complementing cell line (VD60L)

Vero cells
(ATCC CCL-81)

ssODN containing
AAV homology-attB-AAV homology

Cas9+gRNA targeting Vero AAV site
(homology-dependent recombination)

Vero attB cells
chr6 AAV: attB pBRL969: plasmid containing
attP-[4kB HSV$_{VD60}$]-cos$_\lambda$-hisD BxB1 (integrative recombination)
single cell cloning, HisD selection

VD60L cell line
chr6 AAV: 4kB HSV$_{VD60}$-cos$_\lambda$-hisD

*Fig. 1*

Infection with HSV-2:ΔgD::RFP at MOI 0.1 leads to virus propagation and CPE in VD60 and VD60L Clones

```
                             SEQUENCE LISTING

<160> NUMBER OF SEQ ID NOS: 30

<210> SEQ ID NO 1
<211> LENGTH: 118
<212> TYPE: DNA
<213> ORGANISM: Artificial sequence
<220> FEATURE:
<223> OTHER INFORMATION: Vero AAVS1 sequence

<400> SEQUENCE: 1
tctcacaggg aaaactgatg cacagaggaa caatacaaat ggcttgtcga cgacggcggt      60
ctccgtcgtc aggatcattc ggggctagaa aggtgaagac ccaaaattag aactcagg      118

<210> SEQ ID NO 2
<211> LENGTH: 38
<212> TYPE: DNA
<213> ORGANISM: Mycobacterium smegmatis attB

<400> SEQUENCE: 2
ggcttgtcga cgacggcggt ctccgtcgtc aggatcat                              38

<210> SEQ ID NO 3
<211> LENGTH: 48
<212> TYPE: DNA
<213> ORGANISM: Mycobacteriophage Bxb1 attP

<400> SEQUENCE: 3
ggtttgtctg gtcaaccacc gcggtctcag tggtgtacgg tacaaacc                   48

<210> SEQ ID NO 4
<211> LENGTH: 23
<212> TYPE: DNA
<213> ORGANISM: Artificial sequence
<220> FEATURE:
<223> OTHER INFORMATION: forward primer

<400> SEQUENCE: 4
aactcggaaa ctgccatagc agg                                              23

<210> SEQ ID NO 5
<211> LENGTH: 23
<212> TYPE: DNA
<213> ORGANISM: Artificial sequence
<220> FEATURE:
<223> OTHER INFORMATION: reverse primer

<400> SEQUENCE: 5
gtttcttagg gtggtcttct ccg                                              23

<210> SEQ ID NO 6
<211> LENGTH: 20
<212> TYPE: DNA
<213> ORGANISM: Artificial sequence
<220> FEATURE:
<223> OTHER INFORMATION: forward primer

<400> SEQUENCE: 6
gaaagtgcag gagagccagg                                                  20
```

```
<210> SEQ ID NO 7
<211> LENGTH: 24
<212> TYPE: DNA
<213> ORGANISM: Artificial sequence
<220> FEATURE:
<223> OTHER INFORMATION: reverse primer

<400> SEQUENCE: 7
cgattaatat ggctctggtt ctgg                                          24

<210> SEQ ID NO 8
<211> LENGTH: 25
<212> TYPE: DNA
<213> ORGANISM: Artificial sequence
<220> FEATURE:
<223> OTHER INFORMATION: forward primer

<400> SEQUENCE: 8
cacaaaggga gttttccaca cggac                                         25

<210> SEQ ID NO 9
<211> LENGTH: 23
<212> TYPE: DNA
<213> ORGANISM: Artificial sequence
<220> FEATURE:
<223> OTHER INFORMATION: reverse primer

<400> SEQUENCE: 9
cacgacctgc tggttctcag tgg                                           23

<210> SEQ ID NO 10
<211> LENGTH: 100
<212> TYPE: RNA
<213> ORGANISM: Artificial sequence
<220> FEATURE:
<223> OTHER INFORMATION: sgRNA
<220> FEATURE:
<221> NAME/KEY: misc_feature
<222> LOCATION: (1)..(3)
<223> OTHER INFORMATION: Phosphorothiolate bonds
<220> FEATURE:
<221> NAME/KEY: misc_feature
<222> LOCATION: (1)..(3)
<223> OTHER INFORMATION: methylated bases
<220> FEATURE:
<221> NAME/KEY: misc_feature
<222> LOCATION: (100)..(102)
<223> OTHER INFORMATION: Phosphorothiolate bonds
<220> FEATURE:
<221> NAME/KEY: misc_feature
<222> LOCATION: (100)..(102)
<223> OTHER INFORMATION: methylated bases

<400> SEQUENCE: 10
agaggaacaa uacaaauucg guuuuagagc uagaaauagc aaguuaaaau aaggcuaguc    60
cguuaucaac uugaaaaagu ggcaccgagu cggugcuuuu                        100

<210> SEQ ID NO 11
<211> LENGTH: 23
<212> TYPE: DNA
<213> ORGANISM: Artificial sequence
<220> FEATURE:
<223> OTHER INFORMATION: primer

<400> SEQUENCE: 11
ccgctgtttc aacagaaatg acc                                           23
```

```
<210> SEQ ID NO 12
<211> LENGTH: 21
<212> TYPE: DNA
<213> ORGANISM: Artificial sequence
<220> FEATURE:
<223> OTHER INFORMATION: primer

<400> SEQUENCE: 12
ccaactcagt gactgcggtc g                                              21

<210> SEQ ID NO 13
<211> LENGTH: 37
<212> TYPE: DNA
<213> ORGANISM: Artificial sequence
<220> FEATURE:
<223> OTHER INFORMATION: primer ptwB_5996

<400> SEQUENCE: 13
gcggcgtgcg gtacccatgt tcttaattaa atttttc                             37

<210> SEQ ID NO 14
<211> LENGTH: 36
<212> TYPE: DNA
<213> ORGANISM: Artificial sequence
<220> FEATURE:
<223> OTHER INFORMATION: primer ptwB_6082

<400> SEQUENCE: 14
gcgctggcgg taccccctata gtgagtcgta ttatac                             36

<210> SEQ ID NO 15
<211> LENGTH: 33
<212> TYPE: DNA
<213> ORGANISM: Artificial sequence
<220> FEATURE:
<223> OTHER INFORMATION: primer pBRL834_352-attP_F

<400> SEQUENCE: 15
gcgcgcggct tataaggttt gtctggtcaa cca                                 33

<210> SEQ ID NO 16
<211> LENGTH: 34
<212> TYPE: DNA
<213> ORGANISM: Artificial sequence
<220> FEATURE:
<223> OTHER INFORMATION: primer pBRL834_attP_R

<400> SEQUENCE: 16
gcgcgcggct tataaggttt gtaccgtaca ccac                                34

<210> SEQ ID NO 17
<211> LENGTH: 41
<212> TYPE: DNA
<213> ORGANISM: Artificial sequence
<220> FEATURE:
<223> OTHER INFORMATION: primer pYUB328-cosBF

<400> SEQUENCE: 17
gcgcgttagt catgagctag ccgatccgcc ttgttacggg g                        41

<210> SEQ ID NO 18
<211> LENGTH: 45
<212> TYPE: DNA
<213> ORGANISM: Artificial sequence
<220> FEATURE:
<223> OTHER INFORMATION: primer pYUB328-cosBR
```

```
<400> SEQUENCE: 18
gcgcgcgttc gtcatgaatt taaatacgtg tctagatacg tctgc            45

<210> SEQ ID NO 19
<211> LENGTH: 13892
<212> TYPE: DNA
<213> ORGANISM: Artificial sequence
<220> FEATURE:
<223> OTHER INFORMATION: nucleic acid insert in AASV1

<400> SEQUENCE: 19
gtacaggcat ccctgtgaaa gatgcctgag gcctgggcac cagggactcc gaagtccagg      60
cccagcccct cccatttaa cccaggaggc caggcccatc ccctccccca ctcacccagg     120
aggccaggcc ccagcctttc catcctcaga tgcagaagcc caggcccca gcctctcccc      180 attcagaccc aggagtccag gccccagcc cctcctccct gagacccagg agtccaggcc     240
cccagcccct cctccctgag acccaggagt ccaggccaca gccctcctc cctcaaaccc      300 aggagcccag gaccccagct cctcctccct cagacccagg agtccaggct ccagcccctg     360
ctccctcaga tccaggagtc caggctccag ctcctgctcc ctcagaccca ggagtccagg     420
ttccagcccc ctcctccctc agacccagga gcccaggcca cagcccctcc tccctcagac     480
tcagaagccc aggcccccag gtcttctctg ttcagcccta gaatcctgg ctcctagccc      540 ctcctactct agtccccaat cccctagcca ctaaggcagt ggggagggcag gaatgcggga    600 agtgtaccag cctcaccaag tggttgataa aaccacatgg ggtaccctaa gaactcggaa     660
actgccatag caggggggctg atgcttggg acctgcctca agaaggatgc aggagaaaca     720
cagccccagg tggagaaaact ggccgggact caagagtcac ccagagacag tgaccccgtc    780
cttgttttca taggacttag ggtttcagcg ctaaaaccag gctgttatgg gcaaacgtca     840
taagctggtc accccacacc cagacctgac ccaaacccag ctcccttgct tgctggccac     900
gtaacctgag aagggaatcc cctcttccct gaactccagc ccaccccaat actccaggcc     960
tcctgggata ccccgaggag tgagtttgcc aagcagtcac cccacagtgg gaggagaatc    1020
cacctgaaag ccagcctggt ggactgggct ggggcgacct tcgccgggt ccaggccaac     1080 taggtggccc ggggcctctg ggggatgcag gggaaggggg ctcagtctga agagcagagc    1140
caggaacccc tgtagggaaa gtgcaggaga gccaggggca tgggatggtg acgaggaaga    1200
gggacaggga atctgagcgc ctctcctggg cttgccaggg actcaaaccc agaggcccag    1260
agcagggcct tagggaagag ggaccccggg accccgctcc gggcggagga gtatgtccca    1320
gacagcactg gggctcttta aggaaagaag gatggagaaa gagaaggggg tagaggcggc    1380
catgacctgg tgaacaccta ggacgaacca ttctcacaaa gggagttttc cacacggaca    1440
cgccctcctc gccacagccc tgccagggcg gggccggcta ctggccttat ctcacaggga    1500
aaactgatgc acagaggaac aatacaaatg gcttgtcgac gacggcggtc tcagtggtgt    1560
acggtacaaa ccttataatg gttacaaata aagcaatagc atcacaaatt tcacaaataa    1620
agcatttttt tcactgcatt ctagttgtgg tttgtccaaa ctcatcaatg tatcttatca    1680
tgtctgtacc gctgtttcaa cagaaatgac cgcccccggg gggcggtgct gtttgcgggt    1740
tggcacaaaa agacccccgac ccgcgtctgt ggtgttttg gcatcatgtc gccgggcgcc    1800
atgcgtgccg ttgttcccat tatcccattc cttttggttc ttgtcggtgt atcgggggtt    1860
cccaccaacg tctcctccac cacccaaccc caactccaga ccaccggtcg tccctcgcat    1920
gaagccccca acatgaccca gaccggcacc accgactctc ccaccgccat cagccttacc    1980
```

```
acgcccgacc acacaccccc catgccaagt atcggactgg aggaggagga ggaagaggag    2040
gaggggccg gggatggcga acatcttaag gggggagatg ggacccgtga cacccacccc    2100
cagtccccgg gtccagccgt cccgttggcc ggggatgacg agaaggacaa acccaaccgt    2160
cccgtagtcc cacccccccgg tcccaacaac tcccccgcgc ccccgagac cagtcgaccg    2220
aagacacccc ccaccagtat cgggccgctg gcaactcgac ccacgaccca actcccctca    2280
aagggcgac ccttggttcc gacgcctcaa catacccgc tgttctcgtt cctcactgcc    2340
tcccccgccc tggacaccct cttcgtcgtc agcaccgtca tccacacctt atcgtttgtg    2400
tgtattgttg ctatggcgac acacctgtgt ggtggttggt ccagacgcgg gcgacgcaca    2460
caccctagcg tgcgttacgt gtgcctgccg cccgaacgcg ggtagggtat ggggcgggga    2520
tggggagagc ccacacgcgg aaagcaagaa caataaaggc ggcgggatct agttgatatg    2580
cgtctctggg tgttttgggg gtgtggtggg cgcggggcgg tcattggacg ggggtgcagt    2640
taaatacatg cccgggaccc atgaagcatg cgcgacttcc gggcctcgga acccacccga    2700
aacggccaac ggacgtctga gccaggcctg gctatccgga gaaacagcac acgacttggc    2760
gttctgtgtg tcgcgatgtc tctgcgcgca gtctggcatc tggggctttt gggaagcctc    2820
gtgggggctg ttcttgccgc cacccatctg ggacctgcgg ccaacacaac ggaccccta    2880
acgcacgccc cagtgtcccc tcaccccagc ccctggggg gctttgccgt cccctcgta    2940
gtcggtgggc tgtgtgccgt agtcctgggg gcggcgtgtc tgcttgagct cctgcgtcgt    3000
acgtgccgcg ggtgggggcg ttaccatccc tacatggacc cagttgtcgt ataattttt    3060
ccccccccc cttctccgca tgggtgatgt cgggtccaaa ctcccgacac caccagctgg    3120
catggtataa atcaccggtg cgcccccccaa accatgtccg gcagggggat gggggcgaa    3180
tgcggagggc acccaacaac accgggctaa ccaggaaatc cgtggcccccg ccccccaaca    3240
aagatcgcgg tagcccggcc gtgtgacatt atcgtccata ccgaccacac cgacgaatcc    3300
cctaaggggg aggggccatt ttacgaggag gaggggtata acaaagtctg tctttaaaaa    3360
gcagggggtta gggagttgtt cggtcataag cttcagtgcg aacgaccaac taccccgatc    3420
atcagttatc cttaaggtct cttttgtgtg gtgcgttccg gtatgggggg ggctgccgcc    3480
aggttgggg ccgtgatttt gtttgtcgtc atagtgggcc tccatggggt ccgcggcaaa    3540
tatgccttgg cggatgcctc tctcaagatg gccgaccccaa atcgctttcg cggcaaagac    3600
cttccggtcc tggaccagct gaccgaccct ccggggtcc ggcgcgtgta ccacatccag    3660
gcgggcctac cggacccgtt ccagcccccc agcctcccga tcacggttta ctacgccgtg    3720
ttggagcgcg cctgccgcag cgtgctccta aacgcaccgt cggaggcccc ccagattgtc    3780
cgcggggcct ccgaagacgt ccggaaacaa ccctacaacc tgaccatcgc ttggtttcgg    3840
atgggaggca actgtgctat ccccatcacg gtcatggagt acaccgaatg ctcctacaac    3900
aagtctctgg gggcctgtcc catccgaacg cagccccgct ggaactacta tgacagcttc    3960
agcgccgtca gcgaggataa cctggggttc ctgatgcacg ccccgcgtt tgagaccgcc    4020
ggcacgtacc tgcggctcgt gaagataaac gactggacgg agattacaca gtttatcctg    4080
gagcaccgag ccaagggctc ctgtaagtac gccctcccgc tgcgcatccc ccgtcagcc    4140
tgcctctccc cccaggccta ccagcagggg gtgacggtgg acagcatcgg gatgctgccc    4200
cgcttcatcc ccgagaacca gcgcaccgtc gccgtataca gcttgaagat cgccgggtgg    4260
cacgggccca aggcccccata cacgagcacc ctgctgcccc cggagctgtc cgagaccccc    4320
```

```
aacgccacgc agccagaact cgccccggaa gaccccgagg attcggccct cttggaggac    4380
cccgtgggga cggtggcgcc gcaaatccca ccaaactggc acatcccgtc gatccaggac    4440
gccgcgacgc cttaccatcc cccggccacc ccgaacaaca tgggcctgat cgccggcgcg    4500
gtgggcggca gtctcctggc agccctggtc atttgcggaa ttgtgtactg gatgcaccgc    4560
cgcactcgga aagcccccaaa gcgcatacgc ctcccccaca tccgggaaga cgaccagccg    4620
tcctcgcacc agcccttgtt ttactagata cccccccctta atgggtgcgg ggggtcagg    4680 tctgcgggt tgggatggga ccttaactcc atataaagcg agtctggaag ggggaaagg    4740 cggacagtcg ataagtcggt agcggggac gcgcacctgt tccgcctgtc gcacccacag    4800 cttttttcgcg aaccgtcccg tttcgggatg ccgtgccgcc cgttgcaggg cctggtgctc    4860
gtgggcctct gggtctgtgc caccagcctg gttgtccgtg ccccacggtt cagtctggta    4920
tcaaactcat ttgtggacgc cggggccttg gggcccgacg gcgtagtgga ggaagacctg    4980
cttattctcg gggagcttcg ctttgtgggg gaccaggtcc cccacaccac ctactacgat    5040
ggggtcgtag agctgtggca ctaccccatg ggacacaaat gcccacgggt cgtgcatgtc    5100
gtcacggtga ccgcgtgccc acgtcgcccc gccgtggcat ttgccctgtg tcgcgcgacc    5160
gacagcactc acagccccgc atatcccacc ctggagctga atctggccca acagccgctt    5220
ttgcgggtcc ggagggcgac gcgtgactat gccggggtgt acgtgttacg cgtatgggtc    5280
ggggacgcac caaacgccag cctgtttgtc ctggggatgg ccatagccgc cgaaggtact    5340
ctggcgtaca acggctcggc ccatggctcc tgcgacccga aactgcttcc gtcttcggcc    5400
ccgcgtctgg ccccggcgag cgtataccaa cccgcccta acccggcctc cacccccctcg    5460 accaccacct ccaccccctc gaccaccatc cccgctcccc aagcatcgac cacacccttc    5520 cccacggag acccaaaacc ccaacctcac ggggtcaacc acgaacccc atcgaatgcc    5580 acgcgagcga cccgcgactc gcgatatgcg ctaacggtga cccagataat ccagatagcc    5640
atccccgcgt ccattatagc cctggtgttt ctggggagct gtatttgctt tatacacaga    5700
tgtcaacgcc gctaccgacg ctcccgccgc ccgatttaca gcccccagat acccacgggc    5760
atctcatgcg cggtgaacga agcggccatg gcccgcctcg gagccgagct caaatcgcat    5820
ccgagcaccc cccccaaatc ccggcgccgg tcgtcacgca cgccaatgcc ctccctgacg    5880
gccatcgccg aagagtcgga gcccgcgggg gcggctgggc ttccgacgcc ccccgtggac    5940
cccacgacat ccaccccaac gcctccctg ttggtatagg tccacggcca ctggccgggg    6000
gcaccacata accgaccgca gtcactgagt ttaccgtcga cctctagcta gagcttggcg    6060
taatcatggt catagctgtt tcctgtgtga aattgttatc cgctcacaat tccacacaac    6120
atacgagccg gaagcataaa gtgtaaagcc tggggtgcct aatgagtgag ctaactcaca    6180
ttaattgcgt tgcgctcact gcccgctttc cagtcgggaa acctgtcgtg ccagctgcat    6240
taatgaatcg gccaacgcgc ggggagaggc ggtttgcgta ttgggcgctc ttccgcttcc    6300
tcgctcactg actcgctgcg ctcggtcgtt cggctgcggc gagcggtatc agctcactca    6360
aaggcggtaa tacggttatc cacagaatca ggggataacg caggaaagaa catgtgagca    6420
aaaggccagc aaaaggccag gaaccgtaaa aaggccgcgt tgctggcgtt tttccatagg    6480
ctccgccccc ctgacgagca tcacaaaaat cgacgctcaa gtcagaggtg gcgaaacccg    6540
acaggactat aaagatacca ggcgtttccc cctggaagct ccctcgtgcg ctctcctgtt    6600
ccgaccctgc cgcttaccgg atacctgtcc gcctttctcc cttcgggaag cgtggcgctt    6660
tctcaatgct cacgctgtag gtatctcagt tcggtgtagg tcgttcgctc caagctgggc    6720
```

```
tgtgtgcacg aaccccccgt tcagcccgac cgctgcgcct tatccggtaa ctatcgtctt   6780
gagtccaacc cggtaagaca cgacttatcg ccactggcag cagccactgg taacaggatt   6840
agcagagcga ggtatgtagg cggtgctaca gagttcttga agtggtggcc taactacggc   6900
tacactagaa ggacagtatt tggtatctgc gctctgctga agccagttac cttcggaaaa   6960
agagttggta gctcttgatc cggcaaacaa accaccgctg gtagcggtgg ttttttttgtt   7020
tgcaagcagc agattacgcg cagaaaaaaa ggatctcaag aagatccttt gatcttttct   7080
acggggtctg acgctcagtg gaacgaaaac tcacgttaag ggattttggt catgagctag   7140
ccgatccgcc ttgttacggg gcggcgacct cgcgggtttt cgctatttat gaaaattttc   7200
cggtttaagg cgtttccgtt cttcttcgtc ataacttaat gttttatttt aaaataccct   7260
ctgaaaagaa aggaaacgac aggtgctgaa agcgagcttt ttggcctctg tcgtttcctt   7320
tctctgttttt tgtccgtgga atgaacaatg gaagtcaaca aaaagcagac gtatctagac   7380
acgtatttaa attcatgagc ggatacatat ttgaatgtat ttagaaaaat aaacaaatag   7440
gggttccgcg cacatttccc cgaaaagtgc cacctgacgt cgacggatcg ggagatctcc   7500
cgatccccta tggtcgactc tcagtacaat ctgctctgat gccgcatagt taagccagta   7560
tctgctccct gcttgtgtgt tggaggtcgc tgagtagtgc gcgagcaaaa tttaagctac   7620
aacaaggcaa ggcttgaccg acaattgcat gaagaatctg cttagggtta ggcgttttgc   7680
gctgcttcgc gatgtacggg ccagatatac gcgttgacat tgattattga ctaggctttt   7740
gcaaaaagct ttgcaaagat ggataaagtt ttaaacagag aggaatcttt gcagctaatg   7800
gaccttctag gtcttgaaag gagtgcctcg tgaggctccg gtgcccgtca gtgggcagag   7860
cgcacatcgc ccacagtccc cgagaagttg ggggagggg tcggcaattg aaccggtgcc   7920
tagagaaggt ggcgcggggt aaactgggaa agtgatgtcg tgtactggct ccgcttttt   7980
cccgagggtg ggggagaacc gtatataagt gcagtagtcg ccgtgaacgt tcttttcgc   8040
aacgggtttg ccgccagaac acaggtaagt gccgtgtgtg gttcccgcgg gcctggcctc   8100
tttacgggtt atggcccttg cgtgccttga attacttcca cctggctgca gtacgtgatt   8160
cttgatcccg agcttcgggt tggaagtggg tgggagagtt cgaggccttg cgcttaagga   8220
gccccttcgc ctcgtgcttg agttgaggcc tggcctgggc gctggggccg ccgcgtgcga   8280
atctggtggc accttcgcgc ctgtctcgct gctttcgata agtctctagc catttaaaat   8340
ttttgatgac ctgctgcgac gctttttttc tggcaagata gtcttgtaaa tgcgggccaa   8400
gatctgcaca ctggtatttc ggtttttggg gccgcgggcg gcgacgggc ccgtgcgtcc   8460
cagcgcacat gttcggcgag gcggggcctg cgagcgcggc caccgagaat cggacgggg   8520
tagtctcaag ctgccggcc tgctctggtg cctggcctcg cgccgccgtg tatcgccccg   8580
ccctgggcgg caaggctggc ccggtcggca ccagttgcgt gagcggaaag atggccgctt   8640
cccgccctg ctgcagggag ctcaaaatgg aggacgcggc gctcgggaga gcgggcgggt   8700
gagtcaccca cacaaaggaa aagggccttt ccgtcctcag ccgtcgcttc atgtgactcc   8760
acggagtacc gggcgccgtc caggcacctc gattagttct cgagcttttg gagtacgtcg   8820
tctttaggtt ggggggaggg gttttatgcg atggagtttc cccacactga gtgggtggag   8880
actgaagtta ggccagcttg gcacttgatg taattctcct tggaatttgc cctttttgag   8940
tttggatctt ggttcattct caagcctcag acagtggttc aaagtttttt tcttccattt   9000
caggtgtcgt gaggaattag cttggtacta atacgactca ctataggag acccaagctg   9060
```

```
gctaggtaag cttggtaccc atgttcttaa ttaaattttt caaaagtagt tgacaattaa    9120
tcatcggcat agtatatcgg catagtataa tacgactcac tatagggta ccgagctcgg     9180 atccactagt ccagtgtggt ggaattgccc ttagggcaat tctgcagata tgagcttcaa    9240
taccctgatt gactggaaca gctgtagccc tgaacagcag cgtgcgctgc tgacgcgtcc    9300
ggcgatttcc gcctctgaca gtattacccg gacggtcagc gatattctgg ataatgtaaa    9360
aacgcgcggt gacgatgccc tgcgtgaata cagcgctaaa tttgataaaa cagaagtgac    9420
agcgctacgc attacccctg aagagatcgc cgccgccggc gcgcgtctga gcgacgaatt    9480
aaaacaggcg atggccgctg ccgtcaaaaa tattgaaacg ttccattccg cgcagacgct    9540
accgcctgta gatgtggaaa cccagccagg cgtgcgttgc cagcaggtta cgcgtcccgt    9600
cgcgtctgtc ggtctgtata ttcccggcgg ctcggctccg ctcttctcaa cggtgctgat    9660
gctggcgacg ccggcgcgta ttgcgggatg tcagaacgtg gttctgtgct cgccgccgcc    9720
catcgctgat gaaatcctct atgcggcgca actgtgtggc gtgcaggaaa tctttaacgt    9780
cggcggcgcg caggcgattg ccgctctggc cttcggcagc gagtccgtac cgaaagtgga    9840
taaaattttt ggccccggca acgcctttgt aaccgaagcc aagcgtcagg tcagccagcg    9900
cctcgacggc gcggctatcg atatgccagc cgggccgtct gaagtactgg tgatagccga    9960
cagcggcgca acaccggatt tcgtcgcgtc tgacctgctc tcccaggctg agcacggtcc    10020
ggattcccag gtgattctgc tgacgcctga tgctgacatt gcccgcaagg tggcggaggc    10080
ggtagaacgt caactggcgg agctgccgcg cgcggacacc gcccggcagg ccctgagcgc    10140
cagtcgtctg attgtgacca aagatttagc gcagtgcgtc gccatctcta atcagtatgg    10200
gccggaacac ttaatcatcc agacgcgcaa tgcgcgcgat ttggtggatg cgattaccag    10260
cgcaggctcg gtatttctcg gcgactggtc gccggaatcc gccggtgatt acgcttccgg    10320
aaccaaccat gttttaccga cctatggcta tactgctacc tgttccagcc ttgggttagc    10380
ggatttccag aaacggatga ccgttcagga actgtcgaaa gcgggctttt ccgctctggc    10440
atcaaccatt gaaacattgg cggcggcaga acgtctgacc gcccataaaa atgccgtgac    10500
cctgcgcgta aacgccctca aggagcaagc atgagctcga gtctagaggg cccgcggttc    10560
gaaggtaagc ctatccctaa ccctctcctc ggtctcgatt ctacgcgtac cggtcatcat    10620
caccatcacc attgagttta aacccgctga tcagcctcga ctgtgccttc tagttgccag    10680
ccatctgttg tttgccctc ccccgtgcct tccttgaccc tggaaggtgc cactcccact    10740
gtcctttcct aataaaatga ggaaattgca tcgcattgtc tgagtaggtg tcattctatt    10800
ctggggggtg gggtggggca ggacagcaag ggggaggatt gggaagacaa tagcaggcat    10860 gctgggatg cggtgggctc tatggcttct gaggcggaaa gaaccagctg gggctctagg    10920
gggtatcccc acgcgccctg tagcggcgca ttaagcgcgg cgggtgtggt ggttacgcgc    10980
agcgtgaccg ctacacttgc cagcgcccta gcgcccgctc ctttcgcttt cttcccttcc    11040
tttctcgcca cgttcgccgg ctttccccgt caagctctaa atcggggcat ccctttaggg    11100
ttccgattta gtgctttacg gcacctcgac cccaaaaaac ttgattaggg tgatggttca    11160
cgtagtgggc catcgccctg atagacggtt tttcgccctt tgacgttgga gtccacgttc    11220
tttaatagtg gactcttgtt ccaaactgga acaacactca accctatctc ggtctattct    11280
tttgatttat aaggtttgtc tggtcaacca ccgcggtctc cgtcgtcagg atcattcggg    11340
gctagaaagg tgaagaccca aaattagaac tcaggaccaa cttattctga ttttgttttt    11400
ccaaactgct tctcctcttg ggaagtgtaa ggaagcagca gcacccggat cagtgaaatg    11460
```

```
caccagacgg ctgcgccaga gcagctcagg ctccgggaga gggcagcgca gggcggccac    11520
tgagaaccag caggtcgtgc atccccttc cctcccaccc cccgccaagc tctccctccc    11580
aggaccctct ctggctccat cagtgagcaa accctagggg ttctggcggg gagagagagg    11640
tggctccggg aaatgggggt gtgtcaccag ataaggaatc tgcttaaaag gaggtggggg    11700
tcagacccaa tatctggaga ctaggaggga ggaggcctaa ggatgggct tttctgtcac     11760 cagtcctgtc cctagtggct ccactggggg ggggtgagg ggacagataa acgtacccag    11820
aaccagagcc atattaatcg gccctgggaa tagaaggcgg tcccggctct gggacacagg    11880
atcctgtctg gaagtggcca tgggggcccg gcttggagga agagggctag ccgagctctg    11940
ggacccctgc aagatgccgt gacagggcc ggaagagcga gaggtaaagg gggtatggga     12000
gctgcccaaa ttaaagaagt gagaggtgac ccaaatccac aggaggaggg ggtgtccagg    12060
caaagaaagc aagaggatgg agaggtggct aaagccaggg agacagggac tttgggggttg   12120 tccagaaaaa cggtgatgat gcaggcctac aagaagggga ggtggggatg caagggacag    12180
acatcccacg gagaagacca ccctaagaaa cgagagatgg cacaggcccc agaaggagaa    12240
ggaaaaggga acccagcgag tgaagatggc atgggggttg gggtagggag cagagatgcc    12300
cggagaggac ccagacaagg gcaggatccg ctccgaggac accacgtggt gcagcgccga    12360
gaaggaagtg ctctggaaag agcatccttg ggcagcaacg cacagcacag agcaagggga    12420
agagggattg gaggaagctg gaacctgaag gaggtggtgg ggaaggatct gggccgagcc    12480
gtggaggtgg cccaggccac aatctgcagg cagaaagcag cacaggttca ggggagagaa    12540
tgcaggtcag tgaaagcagg acctgcctgg aaaggggaaa cagcgggcca gaggcggcgc    12600
agaagccagt agagctcaaa gtggtccgga ctccggagag agacggccgc gttagagggc    12660
agagtagagg cggcacagca agggcactcg gcggcgagag gggggcagcg caaagtgaca    12720
atggccaggg ccaggagat agaccagagt gagctatggg agctgcctca ggttcaggag     12780 agggcgggc agggagggag acaaagtcca gggccggcta gagaggctca acatcggaag    12840
aggggaagtc gagggaggga tggtaagggg gaccgcaggg gtcagcacag gctggcaaag    12900
ccagggccag ttaaagcgac tccaatgcgg aagacggtag gtcgaagggg actggtaagg    12960
aggcctgggg cagggtggta agcacagagt ggcaaagccc ggggccactt gaagcagccc    13020
caattcggaa gcgggtggt cgaagagggc tggtaagggg gcgctgggac ggggtgtcag     13080
catagggtgg caaagcccag ggctaggaac gacgggcgga tcgagactgg caacggcggc    13140
tcggaaccgg ggaaggagga tgccccaggc ggcgctgcgg agggtgggcc tggccccggg    13200
agacgctgga gggggcgctg acctggtgca gggcgctgat gccgtcggcg ttggtggagt    13260
ccagcacggc gcggcgggc ggcggcgcgg cggggtcgag ctcggcgccg gggccagggt     13320
cggcggcgca cagcatcaga cgcgcttcgt ccaggtcgcc gcccgcacag gccgccagga    13380
actcggcggc gcgctcgaag cggacggtgc gggcgcggcg ctctccgggg ccaggctggg    13440
ggatgtcaca gaggctcctc ggagccagca gccgccgccg ccgccccgg gccagccgcc     13500 gggccatcct ctccggacat cgcaccgccc gccgcccag cgagcgagcg agcgagcgcc     13560
gagccccaac tgccgccgcc gccgcccgcc cgccccgggg gccgccggga actgccgctg    13620
gccccccacc gccccaggga tctcccggcc ccgcccggc gcgccgacgt cacggcgctg     13680
ccccagggtg tgctgggcag gtcgcgggga gcgccggaaa atggagtcca taagcggaag    13740
ttgcccctgg ccactttcag gagtcgctgt gccccgatgc acactgggaa gtccgcagct    13800
```

```
ccgaggcgcc cagtggaaat caccgaatga gggcctcctc cggggaatgc tgggaaatgg    13860
agtctacaga ccggaggggt gccccacggc at                                  13892

<210> SEQ ID NO 20
<211> LENGTH: 100
<212> TYPE: RNA
<213> ORGANISM: Artificial sequence
<220> FEATURE:
<223> OTHER INFORMATION: sgRNA
<220> FEATURE:
<221> NAME/KEY: misc_feature
<222> LOCATION: (1)..(3)
<223> OTHER INFORMATION: Phosphorothiolate bonds
<220> FEATURE:
<221> NAME/KEY: misc_feature
<222> LOCATION: (1)..(3)
<223> OTHER INFORMATION: Methylated bases
<220> FEATURE:
<221> NAME/KEY: misc_feature
<222> LOCATION: (97)..(99)
<223> OTHER INFORMATION: Phosphorothiolate bonds
<220> FEATURE:
<221> NAME/KEY: misc_feature
<222> LOCATION: (97)..(99)
<223> OTHER INFORMATION: Methylated bases

<400> SEQUENCE: 20
ccugcaagau gccgugacag guuuuagagc uagaaauagc aaguuaaaau aaggcuaguc    60
cguuaucaac uugaaaaagu ggcaccgagu cggugcuuuu                          100

<210> SEQ ID NO 21
<211> LENGTH: 100
<212> TYPE: RNA
<213> ORGANISM: Artificial sequence
<220> FEATURE:
<223> OTHER INFORMATION: sgRNA
<220> FEATURE:
<221> NAME/KEY: misc_feature
<222> LOCATION: (1)..(3)
<223> OTHER INFORMATION: Phosphorothiolate bonds
<220> FEATURE:
<221> NAME/KEY: misc_feature
<222> LOCATION: (1)..(3)
<223> OTHER INFORMATION: Methylated bases
<220> FEATURE:
<221> NAME/KEY: misc_feature
<222> LOCATION: (97)..(99)
<223> OTHER INFORMATION: Phosphorothiolate bonds
<220> FEATURE:
<221> NAME/KEY: misc_feature
<222> LOCATION: (97)..(99)
<223> OTHER INFORMATION: Methylated bases

<400> SEQUENCE: 21
ccacccuaag aaacgagaga guuuuagagc uagaaauagc aaguuaaaau aaggcuaguc    60
cguuaucaac uugaaaaagu ggcaccgagu cggugcuuuu                          100

<210> SEQ ID NO 22
<211> LENGTH: 4086
<212> TYPE: DNA
<213> ORGANISM: Chlorocebus sebaeus

<400> SEQUENCE: 22
gtacaggcat ccctgtgaaa gatgcctgag gcctgggcac cagggactcc gaagtccagg    60
cccagcccct cccatttaa ccaggaggc caggcccatc ccctccccca ctcacccagg     120
aggccaggcc ccagcctttc catcctcaga tgcagaagcc caggccccca gcctctccc    180 attcagaccc aggagtccag gccccagcc cctcctccct gagacccagg agtccaggcc   240
```

```
cccagcccct cctccctgag acccaggagt ccaggccaca gcccctcctc cctcaaaccc      300
aggagcccag gaccccagct cctcctccct cagacccagg agtccaggct ccagccctg       360 ctccctcaga tccaggagtc caggctccag ctcctgctcc ctcagaccca ggagtccagg      420
ttccagcccc ctcctccctc agacccagga gcccaggcca cagcccctcc tccctcagac      480
tcagaagccc aggccccag gtcttctctg ttcagcccta gaatcctgg ctcctagccc        540 ctcctactct agtccccaat cccctagcca ctaaggcagt gggagggcag gaatgcggga      600
agtgtaccag cctcaccaag tggttgataa aaccacatgg ggtaccctaa gaactcggaa      660
actgccatag caggggggctg atgcttgggg acctgcctca agaaggatgc aggagaaaca    720
cagccccagg tggagaaact ggccgggact caagagtcac ccagagacag tgacccgtc      780 cttgttttca taggacttag ggtttcagcg ctaaaaccag gctgttatgg gcaaacgtca    840
taagctggtc accccacacc cagacctgac ccaaacccag ctcccttgct tgctggccac    900
gtaacctgag aagggaatcc cctcttccct gaactccagc ccaccccaat actccaggcc   960
tcctgggata ccccgaggag tgagtttgcc aagcagtcac cccacagtgg gaggagaatc   1020
cacctgaaag ccagcctggt ggactgggct ggggcgacct ctcgccgggt ccaggccaac   1080
taggtggccc ggggcctctg ggggatgcag ggaaggggg ctcagtctga agagcagagc    1140
caggaacccc tgtagggaaa gtgcaggaga gccaggggca tgggatggtg acgaggaaga   1200
gggacaggga atctgagcgc ctctcctggg cttgccaggg actcaaaccc agaggcccag   1260
agcagggcct tagggaagag ggaccccggg accccgctcc gggcggagga gtatgtccca   1320
gacagcactg gggctctta aggaaagaag gatgcagaaa gagaagggg tagaggcggc      1380 catgacctgg tgaacaccta ggacgaacca ttctcacaaa gggagtttc cacacggaca    1440 cgccctcctc gccacagccc tgccagggcg gggccggcta ctggccttat ctcacaggga   1500
aaactgatgc acagaggaac aatacaaatt cggggctaga aaggtgaaga cccaaaatta   1560
gaactcagga ccaacttatt ctgattttgt ttttccaaac tgcttctcct cttgggaagt    1620
gtaaggaagc agcagcaccc ggatcagtga aatgcaccag acggctgcgc cagagcagct    1680
caggctccgg gagagggcag cgcagggcgg ccactgagaa ccagcaggtc gtgcatcccc    1740
cttccctccc accccccgcc aagctctccc tcccaggacc ctctctggct ccatcagtga    1800
gcaaacccta ggggttctgg cggggagaga gaggtggctc cggaaatgg gggtgtgtca     1860 ccagataagg aatctgctta aaaggaggtg ggggtcagac ccaatatctg gagactagga    1920 gggaggagc ctaaggatgg ggcttttctg tcaccagtcc tgtccctagt ggctccactg     1980
ggggggggtg gagggacag ataaacgtac ccagaaccag agccatatta atcggccctg     2040
ggaatagaag gcgtcccgg ctctgggaca caggatcctg tctggaagtg gccatggggg    2100
cccggcttgg aggaagaggg ctagccgagc tctgggaccc ctgcaagatg ccgtgacagg    2160
ggccggaaga gcgagaggta aaggggtat gggagctgcc caaattaaag aagtgagagg     2220
tgacccaaat ccacaggagg aggggtgtc caggcaaaga aagcaagagg atggagaggt     2280
ggctaaagcc agggagacag ggactttggg gttgtccaga aaaacggtga tgatgcaggc   2340
ctacaagaag gggaggtggg gatgcaaggg acagacatcc cacggagaag accaccctaa    2400
gaaacgagag atggcacagg ccccagaagg agaaggaaaa gggaacccag cgagtgaaga   2460
tggcatgggg gttggggtag ggagcagaga tgcccggaga ggaccagac aagggcagga    2520 tccgctccga ggacaccacg tggtgcagcg ccgagaagga agtgctctgg aaagagcatc   2580
```

-continued

| | |
|---|---|
| cttgggcagc aacgcacagc acagagcaag gggaagaggg attggaggaa gctggaacct | 2640 |
| gaaggaggtg gtgggaagg atctgggccg agccgtggag gtggcccagg ccacaatctg | 2700 |
| caggcagaaa gcagcacagg ttcaggggag agaatgcagg tcagtgaaag caggacctgc | 2760 |
| ctggaaaggg gaaacagcgg gccagaggcg gcgcagaagc cagtagagct caaagtggtc | 2820 |
| cggactccgg agagagacgg ccgcgttaga gggcagagta gaggcggcac agcaagggca | 2880 |
| ctcggcggcg agagggggc agcgcaaagt gacaatggcc agggcaggg agatagacca | 2940 |
| gagtgagcta tgggagctgc ctcaggttca ggagagggcg gggcagggag ggagacaaag | 3000 |
| tccagggccg gctagagagg ctcaacatcg gaagagggga agtcgaggga gggatggtaa | 3060 |
| gggggaccgc aggggtcagc acaggctggc aaagccaggg ccagttaaag cgactccaat | 3120 |
| gcggaagacg gtaggtcgaa ggggactggt aaggaggcct gggcagggt ggtaagcaca | 3180 |
| gagtggcaaa gcccggggcc acttgaagca gccccaattc ggaagcgggg tggtcgaaga | 3240 |
| gggctggtaa gggggcgctg ggacggggtg tcagcatagg gtggcaaagc ccagggctag | 3300 |
| gaacgacggg cggatcgaga ctggcaacgg cggctcggaa ccggggaagg aggatgcccc | 3360 |
| aggcggcgct gcggagggtg ggcctggccc cgggagacgc tggaggggc gctgacctgg | 3420 |
| tgcagggcgc tgatgccgtc ggcgttggtg gagtccagca cggcgcgggc gggcggcggc | 3480 |
| gcggcggggt cgagctcggc gccggggcca gggtcggcgg cgcacagcat cagacgcgct | 3540 |
| tcgtccaggt cgccgcccgc acaggccgcc aggaactcgg cggcgcgctc gaagcggacg | 3600 |
| gtgcgggcgc ggcgctctcc ggggccaggc tgggggatgt cacagaggct cctcggagcc | 3660 |
| agcagccgcc gccgccgccc ccgggccagc cgccggccca tcctctccgg acatcgcacc | 3720 |
| gcccgcccgc ccagcgagcg agcgagcgag cgccgagccc caactgccgc cgccgccgcc | 3780 |
| cgcccgcccc gggggccgcc gggaactgcc gctggccccc accgccccca gggatctccc | 3840 |
| ggccccgcc cggcgcgccg acgtcacggc gctgcccag ggtgtgctgg gcaggtcgcg | 3900 |
| gggagcgccg ggaaatggag tccataagcg gaagttgccc ctggccactt tcaggagtcg | 3960 |
| ctgtgccccg atgcacactg ggaagtccgc agctccgagg cgcccagtgg aaatcaccga | 4020 |
| atgagggcct cctccgggga atgctgggaa atggagtcta cagaccggag gggtgcccca | 4080 |
| cggcat | 4086 |

<210> SEQ ID NO 23
<211> LENGTH: 20
<212> TYPE: DNA
<213> ORGANISM: Artificial sequence
<220> FEATURE:
<223> OTHER INFORMATION: primer 1231F

<400> SEQUENCE: 23

| | |
|---|---|
| cttgccaggg actcaaaccc | 20 |

<210> SEQ ID NO 24
<211> LENGTH: 20
<212> TYPE: DNA
<213> ORGANISM: Artificial sequence
<220> FEATURE:
<223> OTHER INFORMATION: primer attR

<400> SEQUENCE: 24

| | |
|---|---|
| atgatcctga cgacggagac | 20 |

<210> SEQ ID NO 25
<211> LENGTH: 18

```
<212> TYPE: DNA
<213> ORGANISM: Artificial sequence
<220> FEATURE:
<223> OTHER INFORMATION: primer 1529attB_F

<400> SEQUENCE: 25
gtcgacgacg gcggtctc                                                   18

<210> SEQ ID NO 26
<211> LENGTH: 20
<212> TYPE: DNA
<213> ORGANISM: Artificial sequence
<220> FEATURE:
<223> OTHER INFORMATION: primer 1529attB_R

<400> SEQUENCE: 26
gaccgccttc tattcccagg                                                 20

<210> SEQ ID NO 27
<211> LENGTH: 20
<212> TYPE: DNA
<213> ORGANISM: Artificial sequence
<220> FEATURE:
<223> OTHER INFORMATION: primer 1201F

<400> SEQUENCE: 27
aatctgagcg cctctcctgg                                                 20

<210> SEQ ID NO 28
<211> LENGTH: 20
<212> TYPE: DNA
<213> ORGANISM: Artificial sequence
<220> FEATURE:
<223> OTHER INFORMATION: primer 2471R

<400> SEQUENCE: 28
cccccatgcc atcttcactc                                                 20

<210> SEQ ID NO 29
<211> LENGTH: 40
<212> TYPE: DNA
<213> ORGANISM: Artificial sequence
<220> FEATURE:
<223> OTHER INFORMATION: attL

<400> SEQUENCE: 29
ttgtcgacga cggcggtctc agtggtgtac ggtacaaacc                           40

<210> SEQ ID NO 30
<211> LENGTH: 43
<212> TYPE: DNA
<213> ORGANISM: Artificial sequence
<220> FEATURE:
<223> OTHER INFORMATION: attR

<400> SEQUENCE: 30
ggtttgtctg gtcaaccacc gcggtctccg tcgtcaggat cat                       43
```

ATTB CELL LINE, TRANSGENIC CELL LINES DERIVED THEREFROM, AND METHODS OF MAKING THE SAME

CROSS REFERENCE TO RELATED APPLICATION

This application claims priority to U.S. provisional application 63/082,701 filed on Sep. 24, 2020, which is incorporated by reference herein in its entirety.

STATEMENT OF GOVERNMENT SUPPORT

This invention was made with government support under grant numbers AI017321 and AI057552 awarded by the National Institutes of Health-National Institute of Allergy and Infectious Diseases (NIH-NIAID). The government has certain rights in this invention.

BACKGROUND

Single-cycle infectious viruses defective for one or more essential functions for viral propagation have been developed. A herpes simplex virus-2 (HSV-2) strain deleted in glycoprotein D (ΔgD-2) has been developed to generate a genetically modified, single cycle infectious HSV-2 strain containing a genomic deletion of the gD gene (designated ΔgD-2). In preclinical murine studies, this ΔgD-2 vaccine strain elicited high-titer non-neutralizing Abs that activate Fc gamma receptors (FcγRs) to induce antibody-dependent cell-mediated cytotoxicity (ADCC). Two doses administered subcutaneously completely protected female and/or male mice against lethal vaginal or skin challenge with clinical isolates of HSV-1 and HSV-2 and prevented the establishment of latency. Moreover, vaccination of female mice protected their pups from subsequent HSV challenge in the first week of life.

A single-cycle infectious virus containing a deletion of a gene essential for viral propagation can be efficiently grown in a complementing cell which expresses the viral essential gene as a transgene. The viral transgene can be randomly inserted into the genome of the cell. In the case of ΔgD-2, the virus is grown in the VD60 cell line. VD60 cells produce the gD protein in culture and have been used to effectively complement ΔgD-2 (Cheshenko, N., et al, FASEB J, 2013. 27(7): p. 2584-99). The efficacy of the ΔgD-2 strain cultured in the VD60 cell line as a vaccine to elicit sterilizing immunity against HSV-1 and HSV-2, has been demonstrated (Petro, C. et al, Elife, 2015, 4; Petro, C. D. et al, JCI Insight, 2016, 1(12)). The VD60 cell line was constructed by randomly integrating a 6 kilobase (kb) BamHI J DNA fragment (including the glycoprotein D (gD) gene) from the herpes simplex virus-1 (HSV-1) KOS strain into the genomic DNA of Vero cells using a plasmid containing the BamHI J fragment, a COLE1 plasmid replicon, an ampicillin resistance gene, an SV40 origin of replication, and the *Salmonella* hisD gene as a selectable marker. The VD60 cell line has at least 100 copies of the inserted DNA fragment, but the exact number of copies has been difficult to quantify. Further, the VD60 cell line has been propagated in an unspecified manner and Vero cells have been shown to become carcinogenic.

A new cell line produced and cultured under defined conditions and in which a transgene is stably inserted at a defined position in the cellular genome, is desirable. It would also be beneficial to provide a transgenic cell line which can be effectively used to assess the potency of a virus throughout a process of manufacturing a vaccine including the virus. Further, a transgenic cell line that can be used in a diagnostic assay to detect for the presence of a virus in a sample from a subject, would also be beneficial.

SUMMARY

This disclosure provides a genetically modified mammalian cell comprising a recombination sequence inserted in a target locus on a chromosome of the Vero cell genome, wherein the recombination sequence comprises Bxb1attB sequence from *Mycobacterium smegmatis*.

This disclosure also provides a method of producing a mammalian cell comprising a recombination sequence inserted in a target locus on a chromosome of the mammalian cell genome, wherein the recombination sequence comprises Bxb1attB sequence from *Mycobacterium smegmatis*, the method comprising: providing a complex comprising a guide RNA comprising an oligonucleotide sequence that hybridizes with a target site on the target locus, and a Cas9 endonuclease; providing a single stranded DNA sequence comprising the Bxb1attB sequence; and introducing the complex and the single stranded DNA sequence into the mammalian cell to obtain a mammalian cell comprising the Bxb1attB sequence inserted in the target locus.

This disclosure provides a transgenic mammalian cell comprising a heterologous nucleic acid stably integrated in a target locus on a chromosome of the mammalian cell genome, wherein the heterologous nucleic comprises a heterologous gene configured for expression by the transgenic mammalian cell.

This disclosure also provides a method of producing a transgenic mammalian cell comprising a heterologous nucleic acid stably integrated in a target locus on a chromosome of the transgenic mammalian cell genome, the method comprising: contacting the genetically modified mammalian cell disclosed herein with a heterologous nucleic acid comprising a heterologous gene and a recombination sequence comprising an attP sequence from bacteriophage Bxb1, and an mRNA encoding a bacteriophage Bxb1 integrase and a nuclear localization sequence; and inserting the heterologous nucleic acid at the target locus in the genetically modified mammalian cell by sequence-specific recombination between the Bxb1 attB sequence in the genetically modified mammalian cell and the attP sequence in the heterologous nucleic acid mediated by the Bxb1 integrase, to produce the transgenic mammalian cell.

This disclosure provides a method of propagating a single cycle infectious virus comprising a genome having a deletion of an essential gene, the method comprising: providing a transgenic mammalian cell comprising at least one copy of the essential gene inserted in a target locus on a chromosome of the mammalian cell genome, wherein the transgenic mammalian cell expresses a protein encoded by the essential gene; contacting the transgenic mammalian cell with the single cycle infectious virus; and complementing the single cycle infectious virus with the protein expressed by the transgenic mammalian cell to propagate the single cycle infectious virus.

This disclosure also provides a method of detecting and/or quantifying infectious virus in a sample, the method comprising: providing transgenic mammalian cells comprising a heterologous nucleic acid stably integrated in a target locus on a chromosome of the genome of the mammalian cells, wherein the heterologous nucleic acid comprises a virus promoter operably linked to a reporter gene; contacting the transgenic mammalian cells with the sample, wherein infectious virus present in the sample transactivates the virus promoter and inducing expression of the reporter gene in the transgenic mammalian cells; and quantifying the number of mammalian cells expressing protein encoded by the reporter gene to quantify the infectious virus.

The above described and other features are exemplified by the following figures and detailed description.

BRIEF DESCRIPTION OF THE DRAWINGS

The following figures are exemplary embodiments wherein the like elements are numbered alike.

FIG. 1 illustrates a method of preparing a Vero:attB cell and a method of preparing a VD60L cell line from the Vero:attB cell.

DETAILED DESCRIPTION

Figure 2:
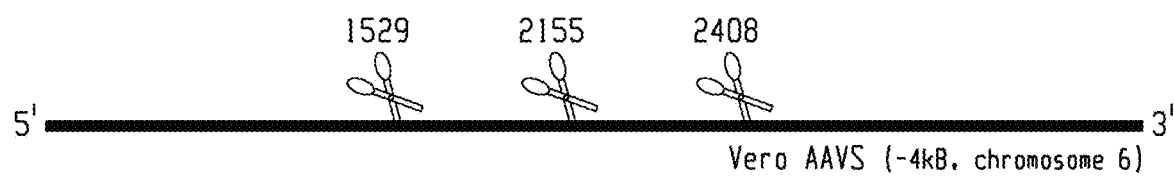
FIG. 2 is a schematic illustration of the Vero AAVS1 site and the location of three candidate guide RNA (gRNAs).

Disclosed herein are mammalian cell lines including the Bxb1 attB sequence from *Mycobacterium smegmatis* (*M. smegmatis*) inserted at a defined location in the chromosome of the cell. In particular, the present disclosure provides a genetically modified Vero cell including the Bxb1 attB sequence at a defined locus in the Vero cell genome.

The mammalian cell lines including the inserted Bxb1 attB sequences can be used, for example, to develop transgenic cell lines which (1) complement the growth and facilitate propagation of single cycle infectious viruses, (2) rapidly detect and/or quantify an amount of viable single cycle infectious virus present in a sample, or (3) can be used as antigen-specific reporter cells for measuring antibody dependent cell-mediated cytotoxicity (ADCC) and/or antibody-dependent cell-mediated phagocytosis. Also disclosed are transgenic mammalian cells derived from the genetically modified mammalian cells, which express at least one heterologous protein. Methods of producing the genetically modified mammalian cells and the transgenic mammalian cells are disclosed as are methods of using these cells.

The term "locus" refers to a specific location on a chromosome. A known locus can contain known genetic information, such as one or more polymorphic marker sites.

A "target locus" is a region of DNA into which a gene or polynucleotide of interest is integrated, e.g., a region of chromosomal or mitochondrial DNA in a cell.

A "nucleic acid construct" or "heterologous nucleic acid" or "vector" as used herein, refers to a nucleic acid sequence, and in particular a DNA sequence, that originates from a source foreign to the particular host cell, or, if from the same source, is modified from its original form. The nucleic acid construct or heterologous nucleic acid is constructed to comprise one or more functional units not found together in nature and is designed to transfer a nucleic acid (or nucleic acids) to a host cell. Examples include circular, double-stranded, extrachromosomal DNA molecules (plasmids), cosmids (plasmids containing COS sequences from lambda phage), viral genomes comprising heterologous (non-native) nucleic acid sequences, and the like. The heterologous nucleic acid can be a DNA sequence. The heterologous nucleic acid includes a DNA sequence of a transgene or heterologous gene. A host cell including the heterologous nucleic acid expresses the heterologous gene. The nucleic acid construct can also be referred to as a vector.

The term "gene" refers to a segment of DNA associated with a biological function. Thus, genes include coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

A "heterologous nucleic acid" refers to a nucleic acid sequence or polynucleotide, and in particular a DNA sequence, that originates from a source foreign to the particular host genome, or, if from the same source, is modified from its original form. The heterologous nucleic acid is constructed to comprise one or more functional units not found together in nature and is designed to transfer a nucleic acid (or nucleic acids) to a host genome. Examples include circular, double-stranded, extrachromosomal DNA molecules (plasmid, shuttle plasmid), cosmids (plasmids containing cos sequences from lambda phage), viral genomes comprising heterologous (non-native) nucleic acid sequences, and the like.

The term "gene" refers to a nucleotide sequence associated with a biological function. Thus, a gene includes a coding sequence and/or the regulatory sequence required for its expression. A gene can also include non-coding DNA segments such as regulatory elements that, for example, form recognition sequences for other proteins. A gene can be obtained from a variety of sources, including cloning from a source of interest or synthesizing from known or predicted sequence information, and may include sequences designed to have desired parameters. A "transgene" or "heterologous gene" refers to a gene that originates from a source foreign to the host cell or, if from the same source, is modified from its original form. Thus, the terms refer to a DNA segment which is foreign or heterologous to the cell, or homologous to the cell but in a position within the host cell nucleic acid in which the element is not ordinarily found. A heterologous gene is expressed to yield a heterologous polypeptide. The term "stably integrated" refers to a heterologous nucleic acid that is incorporated into a host genome, replicates as the cell replicates, and is transferred to progeny. In the present disclosure, the host cell is a Vero cell, and the heterologous nucleic acid is integrated into the Vero cell genome and passed to progeny cells.

A DNA segment (nucleotide sequence) is "operably linked" when placed into a functional relationship with another DNA segment. For example, DNA for a signal sequence is operably linked to DNA for a gene encoding a polypeptide if it is expressed as a preprotein that participates in the secretion of the polypeptide; a promoter or enhancer is operably linked to a coding sequence if it stimulates the transcription of the sequence. In general, DNA sequences that are operably linked are contiguous, and in the case of a signal sequence both contiguous and in reading phase. However, enhancers, for example, need not be contiguous with the coding sequences whose transcription they control. Linking is accomplished by ligation at convenient restriction sites or at adapters or linkers inserted in lieu thereof.

The term "recombinant" when used with reference to a cell indicates that the cell replicates a heterologous nucleic acid, or expresses a peptide or protein encoded by a heterologous nucleic acid. Recombinant cells can contain polynucleotides that are not found within the native (non-recombinant) form of the cell.

A cell has been "transformed" or "transfected" by exogenous or heterologous DNA, e.g. a DNA construct, when such DNA has been introduced inside the cell. The transforming DNA may or may not be integrated (covalently linked) into the genome of the cell.

The term "transgenic" refers to a cell that includes a specific genetic modification that was introduced into the cell, or into an ancestor of the cell. Such modifications can include one or more point mutations, deletions, insertions, or combinations thereof. In the present disclosure, transgenic refers to a cell comprising a heterologous nucleic acid introduced into the cell.

"Recombination sites" are specific polynucleotide sequences that are recognized by the recombinase enzymes described herein. Typically, two different sites are involved (termed "complementary sites"), one present in the target nucleic acid (e.g., a chromosome or episome of a eukaryote) and another on the nucleic acid that is to be integrated at the target recombination site. The terms "attB" and "attP," which refer to attachment (or recombination) sites originally from a bacterial target and a phage donor, respectively, are used herein. The attB site referred to herein is specifically the Bxb1 attB site. The recombination sites can include left and right arms separated by a core or spacer region. Upon recombination between the attB and attP sites, and concomitant integration of a nucleic acid at the target, the recombination sites that flank the integrated DNA are referred to as "attL" and "attR."

The term "promoter" refers to a region of DNA that initiates transcription of a particular gene. The promoter includes the core promoter, which is the minimal portion of the promoter required to properly initiate transcription and can also include regulatory elements such as transcription factor binding sites. The regulatory elements may promote transcription or inhibit transcription. Regulatory elements in the promoter can be binding sites for transcriptional activators or transcriptional repressors. A promoter can be constitutive or inducible. A constitutive promoter refers to one that is always active and/or constantly directs transcription of a gene above a basal level of transcription. An inducible promoter is one which is capable of being induced by a molecule or a factor added to the cell or expressed in the cell. An inducible promoter may still produce a basal level of transcription in the absence of induction, but induction typically leads to significantly more production of the protein.

A "promoter-reporter construct" refers to a DNA vector or plasmid that contains a promoter that drives the transcription of a reporter gene, which in turn, is translated into a reporter protein. The "reporter" or "reporter protein" is a protein whose expression is correlated a cellular event such as to the cellular event, infection, etc. The expression of a reporter protein can be measured using various methods, and depend on the type of reporter protein that is expressed.

The term "transactivation," as used herein refers to the activation of a gene sequence by factors encoded by a regulatory gene, and which is not necessarily contiguous with the gene sequence to which it binds and activates.

A "single cycle infectious virus" also referred to as disabled infectious single cycle (DISC) virus, is a virus defective for one or more essential functions involved in viral genome synthesis, assembly, and/or release of viral particles or re-infection of new host cells. Such viruses are propagated in complementing cell lines that provide the missing gene product or its function in trans.

Disclosed herein is a genetically modified mammalian cell comprising a recombination sequence inserted in a target locus on a chromosome of the mammalian cell genome. The recombination sequence comprises the Bxb1 attB sequence from *Mycobacterium smegmatis* (*M. smegmatis*). A cell line comprising the genetically modified Vero cells is also disclosed.

The type of mammalian cell used is not particularly limited. In an aspect, the cell is an epithelial cell or a lymphoma cell. In an aspect, the epithelial cell is a Vero cell. In an aspect, the lymphoma cell is an RMA cell.

The attB sequence (also referred to herein interchangeably as "attB site") can be inserted into a defined target site on a predetermined target locus in the Vero cell genome. The number of attB sites and target loci are not limited, and the attB site can be inserted in a single target locus in the mammalian cell genome or in a plurality (i.e., more than one) of target loci. The attB site can also be inserted at a single target site in the target locus or at a plurality of sites (i.e., more than one).

In an aspect, the mammalian cell is a Vero cell and the target locus comprises adeno-associated virus integration site 1 (AAVS1), which is located on chromosome 6 of the Vero cell genome. In an aspect, the attB sequence") is inserted in chromosome 6 of the genome of the genetically modified Vero cell between positions 1529 and 1530 of the AAVS1 locus, between positions 2155 and 2156 of the AAVS1 locus, between positions 2408 and 2409 of the AAVS1 locus, or a combination thereof. In an aspect, the AAVS1 locus comprising the recombination sequence has the 4 kilobase sequence of SEQ ID NO 22.

Disclosed herein also is a method of producing the genetically modified mammalian cell comprising an attB sequence from *Mycobacterium smegmatis* inserted in target locus on a chromosome of the Vero cell genome. The method comprises: providing a complex comprising a guide RNA comprising an oligonucleotide sequence that hybridizes with a target site on the target loci and a Cas9 endonuclease; providing a single stranded DNA sequence comprising the attB sequence; and introducing the complex and the single stranded DNA sequence into the mammalian cell to obtain a mammalian cell comprising an attB sequence inserted in the target locus. In an aspect, the Cas9 endonuclease catalyzes a DNA break at the target site in the AAVS1 locus upon hybridizing of the target site with the gRNA.

The generation of the genetically modified mammalian cell and mammalian cell line comprises the use of a CRISPR-Cas9 system. CRISPR refers to the Clustered Regularly Interspaced Short Palindromic Repeats type II system used by bacteria and archaea for adaptive defense. Cas9 refers to CRISPR associated protein 9, which is an endonuclease enzyme. This system enables bacteria and archaea to detect and silence foreign nucleic acids, e.g., from viruses or plasmids, in a sequence-specific manner. In type II systems, guide RNA (gRNA) interacts with Cas9 and directs the nuclease activity of Cas9 to target DNA sequences complementary to those present in the gRNA. gRNA base pairs with complementary sequences in the target DNA, and Cas9 nuclease activity generates a double-stranded break in the target DNA.

In nature, the CRISPR-Cas9 system comprises the Cas9 nuclease and two RNA species: CRISPR RNA (crRNA) and transactivating RNA (tracrRNA). The crRNA includes a nucleotide sequence of a guide RNA that binds to a target DNA sequence and directs Cas9 nuclease activity to the target DNA locus. The crRNA nucleotide sequence includes a portion which is complementary to a genomic DNA sequence as well as additional elements that are complementary to the transactivating RNA (tracrRNA). The tracrRNA hybridizes to the crRNA and binds to the Cas9 protein, to provide an active CRISPR-Cas9 complex. The gRNA can be a single guide RNA (sgRNA) species which combines the tracrRNA and the crRNA fused together in a single RNA molecule, and which can direct Cas9-mediated cleavage of target DNA. An sgRNA species thus contains the sequences necessary for Cas9 binding and nuclease activity and a target sequence complementary to a target DNA of interest. Alternatively, two-part guide RNAs in which the crRNA and the tracrRNA are separate can also be employed.

The term "CRISPR-Cas9 complex" refers to a complex comprising a guide-polynucleotide hybridized to a target-polynucleotide and complexed with a Cas9 protein. In the most straightforward form, the formation of the CRISPR-Cas complex results in cleavage of one or both polynucleotide strands in or near (e.g. within 1 to 20 base pairs from) the target-polynucleotide. The formation of the CRISPR-Cas complex typically results in cleavage of one or both polynucleotide strands 3 base pairs upstream (5') of the target sequence.

In the present disclosure, a CRISPR-Cas system is used to insert an attB site as a recombination site in the genomic DNA of a mammalian cell. The attB site is the Bxb1 attB site from *Mycobacterium smegmatis* into which Bxb1 phage integrates via the Bxb1 attP site. (Barletta, R. G. et al., J Gen Microbiol, 1992. 138(1): p. 23-30; Mediavilla, J. et al., Mol Microbiol, 2000. 38(5): p. 955-70; Ghosh, P. et al., Mol Cell, 2003. 12(5): p. 1101-11; Nkrumah, L. J. et al., at Methods, 2006. 3(8): p. 615-21; and Ohja, A., et al., Cell, 2005. 123(5): p. 861-73)

In aspects of this disclosure, the mammalian cell is a Vero cell. The Vero cell is a kidney epithelial from the Vero cell line that was isolated from the kidney of a normal adult African green monkey (*Chlorocebus Sebaeus*) in 1962 by Yasamura and Kawakita at the Chiba University in Chiba, Japan. The Vero cell is engineered to contain the attB gene integration site at a precisely defined location (target site) in a target locus in the genome. For insertion of the attB gene integration site in Vero cells, a CRISPR-Cas9 system is designed to introduce a double-stranded DNA break at precise locations within the target locus and is transfected into the Vero cells. At least one guide RNA which creates a double stranded DNA break at a target site on the target locus is designed. A CRISPR-Cas9 complex is formed by combining the guide RNA and the Cas9 endonuclease under conditions suitable to form the complex. Once formed, the CRISPR-Cas9 complex is combined with a single stranded DNA sequence comprising the attB site and co-transfected into Vero cells, to resect the damaged DNA (analogous to a "cut and paste" operation). The attB site is thus inserted at the target site on the target locus.

In an aspect, the target locus is adeno-associated virus integration site 1 (AAVS1) locus. The *Chlorocebus Sebaeus* ortholog of the AAVS1 locus (human "safe harbor" locus; Mali et al, Science, 2013 Fe. 15; 339 (6121):823-826) was identified in the Vero cells. A CRISPR-Cas9 system was designed to introduce a double-stranded DNA break at precise locations within AAVS1 locus and transfected into the Vero cells. Three synthetic sgRNAs were designed to create double stranded DNA breaks in the AAVS1 locus: (1) a sgRNA which creates a double stranded break between position 1529 and 1530 of the Vero AAVS1 sequence, (2) a sgRNA which creates a double stranded break between position 2155 and 2156 of the Vero AAVS1 sequence, and (3) a sgRNA which creates a double stranded break between position 2408 and 2409 of the Vero AAVS1 sequence. In an aspect, the sgRNA which creates a double stranded break between positions 1529 and 1530 of the Vero AAVS1 has the sequence of SEQ ID NO 10. In an aspect, the sgRNA that creates a double stranded break between positions 2155 and 2156 of the Vero AAVS1 has the sequence of SEQ ID NO 20. In an aspect, the sgRNA that creates a double stranded break between positions 2408 and 2409 of the Vero AAVS1 has the sequence of SEQ ID NO 21.

In an aspect, the complex (CRISPR-Cas9 complex) is formed by combining a guide RNA specific for the AAVS1 locus and the Cas9 endonuclease under conditions suitable to form the complex. Once formed, the complex is combined with a single stranded DNA sequence (single-stranded DNA repair template) comprising the attB site. The single-stranded DNA sequence containing the attB sequence is co-transfected into Vero cells, along with the CRISPR-Cas9 complex comprising a guide RNA specific for the AAVS1 locus. In an aspect, the single-stranded DNA sequence comprises the 38 nucleotide attB sequence from *M. smegmatis* flanked by Vero AAVS1 upstream and downstream sequences. In an aspect, the single stranded DNA sequence has the sequence of SEQ ID NO. 1. Confirmation that the edited cells contain the attB sequence at the desired location is achieved by PCR and Sanger sequence analysis. The co-transfection can be facilitated by electroporation but is not limited thereto. In an aspect, the attB site is inserted at the target site on the AAVS1 locus. In an aspect, the target site is between positions 1529 and 1530 of the AAVS1 locus, between positions 2155 and 2156 of the AAVS1 locus, between positions 2408 and 2409 of the AAVS1 locus, or a combination thereof.

The genetically modified Vero cell containing the attB recombination site, and the corresponding cell line, are referred to herein as "Vero:attB cell(s)" or "Vero:attB cell line." In an aspect, a Vero:attB cell line comprising the Vero:attB cells is provided. In an aspect, the Vero:attB cell line consists essentially of, or consists of, the Vero:attB cells.

Disclosed herein also is a transgenic mammalian cell comprising a heterologous nucleic acid stably integrated in a target locus on a chromosome of the mammalian cell genome, wherein the heterologous nucleic comprises a heterologous gene configured for expression by the transgenic mammalian. A cell line comprising the transgenic mammalian cells is also disclosed. In an aspect, the transgenic mammalian cell comprises at least one heterologous gene stably inserted in a target locus in the transgenic mammalian cell genome. Expression of the heterologous nucleic acid in the transgenic mammalian cell can be constitutive, inducible, or a combination thereof.

The present disclosure also provides a method of producing a transgenic mammalian cell comprising a heterologous nucleic acid stably integrated in a target locus of the mammalian cell genome. In an aspect, the mammalian cell is a Vero cell and the nucleic acid is integrated in chromosome 6 of the Vero cell genome. The method comprises: providing a genetically modified mammalian cell (e.g., Vero:attB cell) comprising a first recombination sequence inserted in target locus on a chromosome of the mammalian cell genome, wherein the first recombination sequence comprises an attB sequence from M. smegmatis (e.g., Vero:attB cell); providing a heterologous nucleic acid comprising a heterologous gene and a second recombination sequence comprising an attP sequence from bacteriophage Bxb1; providing an mRNA encoding a bacteriophage Bxb1 integrase and a nuclear localization sequence; contacting the genetically modified mammalian cell with the heterologous nucleic acid and the mRNA; and integrating the heterologous nucleic acid into the first recombination sequence in the target locus by sequence-specific recombination mediated by the Bxb1 integrase to produce the transgenic mammalian cell. In an aspect, the contacting comprises introducing the heterologous nucleic acid and the mRNA into the genetically modified Vero cell comprising the first recombination sequence.

In the present disclosure, a Bxb1 integration system is used to generate the transgenic mammalian cell and corresponding mammalian cell line. As disclosed herein, the transgenic mammalian cell is produced by further genetic modification of the genetically modified cell containing the attB gene integration site at a target locus in the cell genome, and into which complementing genes are readily inserted with high efficiency.

The Bxb1 integration system is comprised of: (1) a 38 base pair (bp) attB sequence from M. smegmatis (GGCTTGTCGACGACGGCGGTCTCCGTCGTCAG-GATCAT; SEQ ID NO 2), (2) a 48 base pair attP sequence from bacteriophage Bxb1 (GGTTTGTCTGGTCAAC-CACCGCGGTCTCAGTGGTGTACGGTACAAACC; SEQ ID NO 3), and (3) bacteriophage Bxb1 serine integrase (Bxb1 integrase). The Bxb1 integration system has been demonstrated to be a highly efficient recombination system that only requires the Bxb1 serine integrase enzyme to initiate and complete recombination between its target attB and attP sites. (Xu, et al. BMC Biotechnol, 2013. 13: p. 87).

The Bxb1integrase, which is produced by the Bxb1 mycobacteriophage, mediates recombination between the phage (attP) and bacterial (attB) attachment sites, which are non-identical. Each of the attB and attP target sites contain an integration core flanked by inverted repeats. The recombination facilitated by Bxb1 serine integrase results in genetic modification at the attB target site. The incorporation of the attB sequence in the mammalian cell thus acts as an insertion site for a DNA containing the specific phage attachment (attP) sequence. This allows the cell containing the attB sequence (e.g., Vero:attB) to act as a substrate for integration/insertion of a heterologous nucleic acid molecule containing the specific phage attachment (attP) sequence, mediated by the Bxb1 serine integrase.

Recombination between attB and attP results in the formation of hybrid sites attL and attR that cannot be recombined by Bxb1 integrase without additional components. To mediate excision of a previously integrated nucleic acid sequence, another phage-encoded protein called the recombination directionality factor (RDF), is needed in addition to the Bxb1 integrase. However, in the presence of the Bxb1 integrase alone without the RDF, the integration reaction is unidirectional and does not require host cofactors. Thus, following integration of a heterologous nucleic acid molecule, the transgenic mammalian cell comprises an attL sequence adjacent to a first end of the integrated heterologous nucleic acid and an attR sequence adjacent to a second end of the integrated heterologous nucleic acid molecule.

The attB and/or attP site can be modified, for example by mutation of their respective core sequences, to increase recombination efficiency and/or increase binding affinity of the Bxb1 serine integrase. In an aspect, the attB site has a nucleic acid sequence which is 95%, or 98%, or 99%, or 100% homologous to SEQ ID NO 2. In an aspect, the attP site has a nucleic acid sequence which is 95%, or 98%, or 99%, or 100% homologous to SEQ ID NO 3.

The attL site or sequence has a nucleic acid sequence of GGCTTGTCGACGACGGCGGTCTCAGTGGTGT-ACGGTACAAACC (SEQ ID NO 29). In an aspect, the attR site or sequence has a nucleic acid sequence of GGTTTGTCTGGTCAACCACCGCGGTCTC CGTCGTCAGGATCAT (SEQ ID NO 30).

To facilitate site-specific integration of the heterologous nucleic acid in the genomic DNA of mammalian cells containing the attB site (attB-containing cell), the attB-containing cells are contacted with Bxb1 integrase and a heterologous nucleic acid comprising the HSV gene and the attP sequence. The Bxb1 integrase is introduced into the attB-containing cells by way of an mRNA sequence encoding the Bxb1 integrase, which is transfected into the cell. Specifically, the heterologous nucleic acid (DNA sequence) and an mRNA sequence encoding the Bxb1 integrase are co-transfected into the attB-containing cell. The mRNA encoding the Bxb1 integrase can also include a sequence encoding a nuclear localization sequence/signal (NLS). The NLS is a short peptide (e.g., 4-20 amino acids) that acts as a signal to mediate the transport of protein (synthesized Bxb1 integrase) from the cytoplasm into the nucleus. NLS sequences are known, and include those that present within viral proteins such as those from HIV-2, influenza virus, adenovirus, and/or simian virus-40 (SV-40). In an aspect, the NLS is a 10 amino acid peptide that targets nuclear localization. In an aspect, the NLS is from SV-40.

In an aspect, the mRNA sequence encodes the Bxb1 integrase and the nuclear localization sequence. In an aspect, the mRNA is synthesized in vitro from a plasmid containing the Bxb1 integrase gene and an SV40 nuclear localization sequence downstream of a promoter a T7 promoter. In an aspect, the attP-containing plasmid is amplified in E. coli. When the heterologous nucleic acid including the attP site is co-transfected with the mRNA, the mRNA is translated into the Bxb1 integrase with a nuclear localization peptide on the amino terminus, allowing entry of the Bxb1 integrase into the nucleus with the heterologous nucleic acid and resulting in the attB/attP integration reaction.

The target locus and/or target site for insertion/integration of the heterologous nucleic acid is defined by the position at which the attB sequence is integrated in the genome of the mammalian cell. The target site and/or target locus of the attB sequence, are not limited. In an aspect, the heterologous nucleic acid is inserted in a single target locus or in a plurality of target loci. In an aspect, the heterologous nucleic acid is inserted at a single target site in a target locus or at a plurality of sites in the target locus.

In an aspect, the mammalian cell is a Vero cell and the target locus for insertion/integration of the heterologous nucleic acid comprises the AAVS1 locus on chromosome 6 of the Vero:attB cell. In particular, the heterologous nucleic acid is integrated/inserted at a specific position (target site) within the AAVS1 locus. In an aspect, the heterologous nucleic acid can be inserted between positions 1529 and 1530 of the AAVS1 locus, between positions 2155 and 2156 of the AAVS1 locus, between positions 2408 and 2409 of the AAVS1 locus, or a combination thereof. In an aspect, the heterologous nucleic acid is inserted between positions 1529 and 1530 of the AAVS1 locus.

The heterologous nucleic acid is designed to facilitate its insertion at the attB site in the attB-containing cell. To do so, the heterologous nucleic acid comprises a recombination sequence comprising the attP sequence from bacteriophage Bxb1.

The heterologous nucleic acid is also designed to facilitate expression of the heterologous gene following integration in the genome of the mammalian cell. In an aspect, the heterologous nucleic acid comprises a promoter operably linked to the heterologous gene. The promoter drives the synthesis of a primary transcript from the heterologous gene. Exemplary promoters include inducible promoters, constitutive promoters, tissue-specific promoters, and synthetic promoters.

Other useful elements can also be included in the heterologous nucleic acid. For example, the heterologous nucleic acid can further include a gene encoding a selectable marker, a bacterial origin of replication, a viral origin of replication, or a combination thereof. The heterologous nucleic acid can also include other sequences that can be used to modulate transgene expression or improve cloning of antigen, like a WPRE, an *E. coli* cosmid sequence (a cos sequence), a bacterial promoter, a transmembrane domain, and/or a polyadenylation (polyA) signal. A transmembrane domain, such as the platelet-derived growth factor receptor (PDGFR) transmembrane domain, may be fused to or used in conjunction with the heterologous gene to enable expression of the heterologous gene product on the cell membrane surface. A polyA signal sequence promotes polyadenylation and transcription termination and is located downstream of the heterologous gene. Exemplary polyA signal sequences include the SV40 poly(A) signal, the bovine growth hormone polyadenylation signal (bGHpA), human growth hormone polyadenylation signal (hGHpA), immunoglobulin kappa signal, and rabbit beta globin polyadenylation signal (rbGlob), but is not limited thereto.

Expression of the heterologous gene can be qualitatively and/or quantitatively assessed based on expression of a gene encoding a selectable marker (also referred to herein as "reporter gene" and "reporter protein"). In an aspect, the heterologous nucleic acid further comprises a selectable marker operably linked to the heterologous gene. The gene encoding the selectable marker can be inserted upstream and/or downstream of the gene encoding the heterologous polypeptide. In an aspect, the selectable marker gene is inserted downstream of the gene encoding the heterologous polypeptide. In an aspect, the selectable marker is operably linked to the promoter and to the gene encoding the heterologous polypeptide. The selectable marker can induce a visually identifiable characteristic distinguishable from the cell in which it is being expressed and which can be readily measured. Alternatively, the selectable marker can be one which confers a host cell with the ability to grow in the presence of a selective agent, or one which confers a host cell with the ability to grow in the absence of a required nutrient.

Non-limiting examples of genes encoding selectable markers include a gene encoding β-galactosidase (lacZ), a fluorescent protein, a luminescent protein, hisD, or a combination thereof. In an aspect, the selectable marker is a gene encoding hisD from *Salmonella typhimurium.*

In an aspect, the selectable marker can be the *Salmonella typhimurium* hisD gene. Advantageously, the heterologous nucleic acid does not contain an antibiotic resistance marker, an SV40 sequence, or a combination thereof. Accordingly, in an aspect, the transgenic mammalian cell also does not contain an antibiotic resistance marker, an SV40 sequence, or a combination thereof. In an aspect, the SV40 sequence is the SV40 origin of replication.

In an aspect, the heterologous nucleic acid is a plasmid. In an aspect, the plasmid comprises the attP site, a promoter, a heterologous gene operably linked to the promoter, and a selectable marker (e.g., the hisD gene). The plasmid is transfected into the attB-containing cell and integrated into the genome by site specific recombination between the attB site and the attP site. In an aspect, the plasmid does not comprise or contain an antibiotic resistance marker, an SV40 sequence, or a combination thereof. In an aspect, the plasmid is devoid of (does not comprise or contain) an antibiotic resistance marker and an SV40 sequence.

The present disclosure provides a transgenic mammalian cell comprising a heterologous nucleic acid stably integrated in a target locus on a chromosome of the mammalian cell genome, wherein the heterologous nucleic comprises a heterologous gene configured for expression by the transgenic mammalian cell. In an aspect, the transgenic mammalian cell comprises at least one copy of the heterologous nucleic acid inserted in the target locus. In an aspect, the transgenic mammalian cell comprises 1 to 50 copies, or 1 to 20 copies, or 1 to 10 copies of the heterologous nucleic acid inserted in the target locus.

In an aspect the heterologous nucleic acid comprises a heterologous gene comprising a virus gene, a reporter gene, or a combination thereof.

The cell lines including the inserted Bxb1 attB sequences can be used to develop transgenic cell lines which complement the growth and facilitate propagation of single cycle infectious viruses. In an aspect, the heterologous nucleic acid comprises a virus gene. The virus gene can be from a DNA virus, an RNA virus, or a combination thereof. The virus gene can comprise a single virus gene or a combination of virus genes. The virus gene is operably linked to a promoter which drives the synthesis of a primary transcript from the virus gene. The transgenic mammalian cell and corresponding cell line stably express the virus genes encoded by the heterologous nucleic acid. In an aspect, the promoter is a constitutive promoter and the virus gene is constitutively expressed by the transgenic mammalian cell. In an aspect, the promoter comprises a CMV promoter, a CAG promoter, an elongation factor 1 alpha (EF1α) promoter, a phosphoglycerate kinase 1 (PKG1) promoter, a ubiquitin C (Ubc) promoter, a beta actin promoter, or a combination thereof.

The virus gene can comprise a gene from herpes simplex virus-1 (HSV-1), herpes simplex virus-2 (HSV-2), cytomegalovirus, rotavirus, smallpox, poliovirus, rabies virus, reovirus, Japanese encephalitis virus, hemorrhagic fever virus, measles virus, influenza virus, middle-eastern respiratory syndrome coronavirus, Zika virus, dengue virus, SARS-CoV2, influenza A virus, or a combination thereof. The virus gene is not limited and can be any virus gene which can be expressed in a mammalian cell.

The virus gene can be an essential gene, a non-essential gene, or a combination of an essential gene and a non-essential gene. An "essential gene" refers to a gene encoded by the virus genome that is required for replication of the virus and production of new infectious viral particles or virions (growth of the virus). In an aspect, the virus gene is an essential gene.

In an aspect, the heterologous nucleic acid comprises an HSV gene. The HSV gene can be a single HSV gene or a combination of HSV genes. In an aspect, the heterologous nucleic acid comprises at least one HSV gene. In an aspect, the heterologous nucleic acid comprises at least two, or at least three, or at least four HSV genes. The HSV gene can be from herpes simplex virus-1 (HSV-1), herpes simplex virus-2 (HSV-2), or a combination thereof (e.g., a gene from HSV-1 and a gene from HSV-2). In an aspect, the HSV gene comprises an HSV essential gene or a combination of an HSV essential gene and an HSV non-essential gene. The HSV genome encodes approximately ninety different genes that can be classified as either essential or non-essential. In an aspect, the transgenic mammalian cell, as well as the corresponding cell line, stably expresses the HSV gene encoded by the heterologous nucleic acid and supports (complements) the replication of a single cycle infectious HSV virus comprising a genomic modification of the corresponding HSV gene. In an aspect, the genomic modification is a full or partial deletion of the HSV gene in the HSV genome.

Non-limiting examples of essential HSV genes comprise genes encoding for proteins contained in the lipid envelope of the virus, such as, glycoprotein B (gB), glycoprotein C (gC), glycoprotein D (gD), glycoprotein E (gE), glycoprotein G (gG), glycoprotein H (gH), glycoprotein I (gI), glycoprotein J (gJ), glycoprotein K (gK), glycoprotein L (gL), glycoprotein M (gM), glycoprotein N (gN), UL20, UL45, US9, or a combination thereof. In an aspect, the HSV gene comprises gD gene, gG gene, gI gene, gJ gene, or a combination thereof. In an aspect, the HSV gene comprises glycoprotein D. In an aspect, the HSV gene comprises glycoprotein D gene, glycoprotein G gene, glycoprotein I gene, glycoprotein J gene, or a combination thereof. In an aspect, the HSV gene comprises a herpes simplex virus-1 (HSV-1) glycoprotein D gene, a herpes simplex virus-2 (HSV-2) glycoprotein D gene, or a combination thereof.

In an aspect, the transgenic mammalian cell is a Vero cell and comprises the HSV-1 glycoprotein D gene, the HSV-2 glycoprotein D gene, or a combination thereof. In an aspect, the heterologous nucleic acid is a 13.9 kB sequence comprising the HSV-1 gD, gD, gJ, and gI genes and has a sequence corresponding to SEQ ID NO 19. These transgenic Vero cells comprising the HSV-1 glycoprotein genes inserted at the attB site, and the corresponding cell line, are referred to herein as "VD60L cells" or "VD60L cell line." In an aspect, the VD60L cell line consists essentially of, or consists of, VD60L cells. The VD60L cells stably express the HSV-1 glycoprotein genes and complements a genetically modified, single cycle infectious HSV-1 strain containing a genomic deletion of one or more of these genes. The genomic deletion can be a full or partial deletion. In an aspect, the VD60L cells complement a single cycle infectious HSV-2 strain containing a genomic deletion of the HSV-2 gD gene (ΔgD-2). Since the VD60L cells and corresponding cell line are produced and maintained under defined conditions, any potential safety concerns associated with production of the virus are minimized.

Disclosed herein is a method of propagating a single cycle infectious virus comprising a genome having a deletion of an essential gene, the method comprising: providing a transgenic Vero cell comprising at least one copy of the essential gene inserted in a target locus on a chromosome of the Vero cell genome, wherein the transgenic Vero cell expresses a protein encoded by the essential gene; contacting the transgenic Vero cell with the single cycle infectious virus; and complementing the single cycle infectious virus with the protein expressed in the transgenic Vero cell to propagate the single cycle infectious virus. In an aspect, the target locus comprises adeno-associated virus integration site 1 (AAVS1) on chromosome 6 of the Vero cell genome.

Single cycle infectious viruses are viruses that have been genetically modified to prevent the formation of mature virions capable of spreading to neighboring uninfected cells. Single cycle infectious viruses are unable to form infectious viral particles following initial infection of a host cell and undergo only a single round of replication and infection. The genetic modification is typically made to an essential viral gene, and can be a complete or partial deletion of the viral gene, or a mutation thereto, which effectively prevents the formation of mature virions in a host cell. As a result, the single cycle infectious virus can only establish a lytic infection and propagate if the missing gene is supplied in trans by an engineered cell (complementing cell). In an aspect, the transgenic mammalian cell stably expresses a viral gene and phenotypically complements the replication of a single cycle infectious virus comprising a genome having a genetic modification (e.g., deletion) of the same gene. As a result of this complementation, the single cycle infectious virus is able to replicate and produce new infectious viral particles in the transgenic mammalian cell. Since the transgenic mammalian cells and corresponding transgenic mammalian cell line are produced and maintained under defined conditions, any potential safety concerns associated with production of a single cycle infectious virus are minimized.

In an aspect, the single cycle infectious virus comprises herpes simplex virus-1 (HSV-1), herpes simplex virus-2 (HSV-2), cytomegalovirus, rotavirus, smallpox, poliovirus, rabies virus, reovirus, Japanese encephalitis virus, hemorrhagic fever virus, measles virus, influenza virus, middle-eastern respiratory syndrome coronavirus, Zika virus, SARS-CoV2, or a combination thereof.

In an aspect, the single cycle infectious virus is an single cycle infectious HSV (HSV-1 or HSV-2), comprising a partial or complete deletion of an essential gene or a combination of an essential gene and a non-essential gene. In an aspect, the deleted HSV essential gene comprises gB, gC, gD, gE, gG, gH, gI, gJ, gK, gL, gM, gN, UL20, UL45, US9, or a combination thereof. In an aspect, the deleted HSV gene comprises gD, gG, gI, gJ, or a combination thereof. In an aspect, the HSV gene comprises glycoprotein D. In an aspect, the HSV gene comprises gD, gG, gI, and gJ. In an aspect, the HSV gene comprises a herpes simplex virus-1 (HSV-1) glycoprotein D gene, a herpes simplex virus-1 (HSV-2) glycoprotein D gene, or a combination thereof.

In an aspect, the single cycle infectious HSV is a single cycle infectious HSV-1 or HSV-2 comprising a deletion of the glycoprotein D gene in the genome of the HSV-1 or HSV-2. In an aspect, the single cycle infectious HSV is an single cycle infectious HSV-2. In an aspect, the single cycle infectious virus comprises HSV-2 comprising a deletion of the gD gene in the genome of the HSV-2. In an aspect, the single cycle infectious virus HSV is the ΔgD-2 strain, having a genomic deletion of the gD gene. In an aspect, the heterologous nucleic acid gene is stably integrated in the genome of transfected Vero cell and comprises a herpes simplex virus-1 (HSV-1) glycoprotein D gene, a herpes simplex virus-1 (HSV-2) glycoprotein D gene, or a combination thereof. A VD60 cell line capable of complementing a single cycle infectious virus HSV such as the ΔgD-2 strain, was first developed by David Johnson in 1988 (Ligas M W & Johnson D C (1988), *J Virol* 62(5):1486-1494). In brief, a 6 kb BamH1 fragment from the KOS strain of HSV-1 was ligated into an *E. coli* plasmid containing a hisD gene and then transfected into Vero cells. A histidinol-resistant clone was isolated that allowed for facile complementation of the ΔgD-2::GFP virus (Cheshenko N, et al. (2014) *J Virol* 88(17):10026-10038; Petro C, et al. (2015), *Elife* 4). Although VD60 cells complement the ΔgD-2 virus, it is desirable to provide a new cell line (VD60L) that not only complements, but also minimizes the likelihood of illegitimate or homologous recombination. The VD60L cells can be used both to propagate the ΔgD-2 virus as well as to detect the number of viable single cycle virus infectious particles (e.g., ΔgD-2) present in a sample (e.g., an aliquot of a vaccine preparation).

The ΔgD-2 propagated in the transgenic Vero cell line can be formulated for administration to a subject. The efficacy of the ΔgD-2 strain cultured in the VD60 cell line as a vaccine to elicit sterilizing immunity against HSV-1 and HSV-2 has been demonstrated (Petro, C. et al, Elife, 2015, 4; Petro, C. D. et al, JCI Insight, 2016, 1(12); WO 2015/134368). Accordingly, the ΔgD-2 propagated in the transgenic Vero cell line can be used to treat or prevent an HSV-1 infection, an HSV-2 infection, or an HSV-1 and HSV-2 coinfection in a subject. In an aspect, the ΔgD-2 propagated in the transgenic Vero cell line can be used to treat or prevent a disease caused by an HSV-1 infection, an HSV-2 infection, or an HSV-1 and HSV-2 coinfection in a subject.

In an aspect, the contacting of the cultivated (cultured) transgenic mammalian cell with the single cycle infectious virus comprises adding the single cycle infectious virus to the cultivated transgenic mammalian cells under conditions that facilitate infection of the transgenic mammalian cells with the single cycle infectious virus. The conditions used to infect the transgenic mammalian cells with the single cycle infectious virus are not limited, and any suitable conditions can be used. In an aspect, the transgenic mammalian cells are VD60L cells.

In an aspect, the propagating of the single cycle infectious virus in the transgenic mammalian cells further comprises culturing the infected transgenic mammalian cells for a period of time and under conditions (e.g., temperature, relative humidity, $CO_2$ atmosphere) suitable to maximize production of the single cycle infectious HSV. The conditions resulting in maximum production of the single cycle infectious virus vary and are not limited, and can comprise, for example, culturing the infected cells at a temperature of 37° C., in a 5% $CO_2$ atmosphere, for a determined time period.

In an aspect, the transgenic mammalian cell comprises a selection marker encoded by the inserted heterologous nucleic acid. In an aspect, the method further comprises cultivating the transgenic mammalian cell in a selection medium. In an aspect, the transgenic mammalian cell comprises hisD as a selection marker and the selection medium comprises histidinol. The amount of histidinol in the culture medium is not limited and can be determined by the person of skill in the art without undue experimentation.

The genetically modified mammalian cells including the inserted Bxb1 attB sequences (attB-containing cells) can also be used to develop transgenic mammalian cell lines which rapidly detect and/or quantify an amount of viable single cycle infectious virus present in a sample. Such a transgenic mammalian cell line contains a reporter gene fused to a viral promoter, and the reporter gene is expressed upon infection of the cell with virus capable of activating the virus promoter in trans. In an aspect, the heterologous gene is a reporter gene operably linked to a virus promoter.

The reporter gene can encode a fluorescent protein, a luminescent protein, or a combination thereof. Non-limiting examples include luciferase, nanoluciferase (nanoLuc), beta-lactamase, alkaline phosphatase, green fluorescent protein (GFP), enhanced green fluorescent protein (EGFP), red fluorescent protein (RFP), Venus, monomeric Infrared Fluorescent Protein (mIFP), Long Stokes Shift monomeric Orange (LssmOrange), Red Fluorescent Protein (RFP), Tag Red. Fluorescent Protein 657 (TagRFP657), monomeric Orange2 (mOrange4 monomeric Apple (mApple), Sapphire, monomeric Tag Blue Fluorescent Protein (mTagBFP2), tdTomato, monomeric Cherry (mCherry), Yellow Fluorescent Protein (YFP), Enhanced Yellow Fluorescent Protein (EYFP), monomeric Cerulean3 (mCerulean3), Green Fluorescent Protein (GFP), Enhanced Green Fluorescent Protein (EGFP), or a combination thereof. However, the reporter genes are not limited thereto and other suitable reporter genes can also be used.

The virus promoter can be operably linked to the reporter gene such that transactivation of the virus promoter results in expression of the reporter protein encoded by the reporter gene. For example, the heterologous nucleic acid can comprise a promoter-reporter construct. In particular, the promoter is transactivated by factors encoded by a regulatory gene of a virus and which are specific for the viral promoter. The promoter is an inducible promoter and is turned on in the presence of a virus encoding the genes capable of turning on the promoter. Thus, when the transgenic mammalian cell is contacted with, and infected by, a virus capable of transactivating the virus promoter, the virus transactivates the virus promoter and induces expression of the reporter gene in the transgenic mammalian cells. The number of infectious virus particles present in a sample can thus be measured by quantifying the number of cells expressing the reporter protein. The expression of the reporter protein in infected cells can be compared to background levels of fluorescence detected in uninfected cells. Expression of the reporter protein can be detected using any method suitable for detecting and quantifying immunofluorescent cells, for example, methods such as fluorescence activated cell sorting (FACS), immunofluorescent microscopy.

In an aspect, the virus promoter is from HSV-1, HSV-2, cytomegalovirus, rotavirus, smallpox, poliovirus, rabies virus, reovirus, Japanese encephalitis virus, hemorrhagic fever virus, measles virus, influenza virus, middle-eastern respiratory syndrome coronavirus, dengue virus, Zika virus, SARS-CoV2, or a combination thereof and is transactivated (induced) by infection of the transgenic mammalian cell with the respective virus.

In an aspect, the virus promoter is a promoter from HSV-1 or HSV-2. The HSV-1 or HSV-2 promoter can include the ICP0 promoter, the ICP4 promoter, the ICP27 promoter, the ICP8 promoter, the thymidine kinase (TK) promoter, the virion protein 5 (VP5) promoter, or a combination thereof.

Gene expression during herpes simplex virus type 1 (HSV-1) replication is temporally regulated. The early phase of gene expression takes place before viral DNA replication and most early viral mRNAs continue to be expressed throughout infection. The early phase of gene expression can be divided into two stages: the α or immediate-early (IE) stage, which occurs in the absence of de novo protein synthesis, and the β or true early (E) stage, which requires the action of at least some IE genes. The late stage of HSV-1 gene expression can also be divided into two stages: the βγ or "leaky" late genes, which can be marginally detected before viral DNA replication, and the γ late (L) mRNAs, which can be detected only after viral DNA synthesis.

After entering the cell, HSV capsid and tegument gradually loosen and separate. The nucleocapsids are transported to the nuclear pore, releasing the viral DNA to the nucleus; VP16 protein, present in the tegument of the viral particle, itself does not possess a nuclear localization signal but is transported to the nucleus by cellular factor HCF-1. VP16 binds to the immediate-early (IE) gene promoter to stimulate the transcription of IE genes as a transactivating factor that acts specifically on IE genes. HSV IE gene transcription is mediated by viral (VP16) and cellular (i.e., HCF-1, Oct-1, SP1, and GABP) transcription factors that assemble a potent transcription enhancer complex. The core domain interacts with two cellular proteins, Oct-1 and HCF-1, to form a DNA-binding complex at specific cis-regulatory elements in the viral IE gene promoters. A primary driver of IE expression is the cellular coactivator HCF-1. HCF-1 plays a key role in modulating the chromatin assembled on the IE genes as part of a complex containing histone demethylases (JMJD2/KDM4 and LSD1/KDM1A) and histone H3K4 methyltransferases (SETD1A and MLL1/KMT2A). This complex limits the assembly of heterochromatin at IE promoters and promotes the transition to an active euchromatic chromatin state. HCF-1 protein is a central regulatory component for both the lytic infectious cycle and for reactivation from latency. (Vogel and Kristie, 2013—doi.org/10.3390/v5051272; Liang et al., 2009-DOI: 10.1038/nm. 2051, 2013-DOI: 10.1126/scitranslmed. 3005145).

Some cellular proteins and viral proteins can regulate the transcription of IE genes mediated by VP16, for example, heat-shock protein 90α (Hsp90α). The viral tegument proteins pUL14, VP11/12 (encoded by UL46), and VP13/14 (encoded by UL47) can enhance the efficiency of IE gene transcription mediated by VP16, which may play the same role in promoting nuclear input of VP16 (Lee et al., 2008; Yamauchi et al., 2008; Hernandez Duran et al., 2019). Another tegument protein, the protein kinase US3, can regulate the release of the virus and promote the dissociation of VP11/12, VP13/14, and VP16 from tegument by phosphorylation, allowing entry into the nucleus as early as possible to initiate the transcription of viral genes (Kato and Kawaguchi, 2018; Hernandez Duran et al., 2019). The HSV-1IE protein ICP22 can inhibit the transcription of IE genes, but VP16 can relieve the inhibition. Although there is no direct interaction between VP16 and ICP22, ICP22 can interact with various transcription factors that also bind to VP16 (Cun et al., 2009; Guo et al., 2012). Therefore, the transcriptional regulation of IE genes by VP16 and ICP22 may be achieved through some unknown action of both and related transcription factors.

The transgenic mammalian cell comprising a reporter gene as the heterologous gene can be used to detect and/or quantify virus present in a sample and/or to determine the infectivity of a stored virus sample. The present disclosure provides a method of detecting and/or quantifying infectious virus in a sample using a cell-based reporter assay. The cell-based reporter assay and detection method utilize, for example, transgenic mammalian cells comprising a heterologous nucleic acid stably integrated in a target locus of the mammalian cell, wherein the heterologous nucleic acid comprises a virus promoter operably linked to a reporter gene.

In general, the use of epithelia cells such as Vero cells for testing a sample for the presence of infectious (i.e., live) virus, quantifying the amount of infectious virus present in a sample known to contain the virus, and/or determining the infectivity of a stored virus sample, is based on a plaque assay. The plaque assay includes exposing the Vero cells to a sample containing the virus under conditions suitable to facilitate virus infection of the cells, waiting a period of time to determine whether virus propagates in the cells to produce new infectious particles, and quantifying the infectious particles by counting individual plaques. In the case of a single cycle infectious virus, a complementing cell expressing the gene missing from the single cycle infectious virus is used in such an assay. However, such methods of measuring the potency of a virus are both time and labor intensive. A method of quantifying the amount of a virus in a sample which can be conducted within a relatively short period of time would be highly advantageous.

The present disclosure provides a cell based reporter assay for quantifying infectious virus in a sample. The cell based reporter assay utilizes transgenic mammalian cells comprising a heterologous nucleic acid comprising a promoter-reporter construct. The cell-based reporter assay can be used to detect the presence of infectious virus in a sample and for measuring virus infectivity (potency). The cell-based reporter assay can also be used to test a biological sample for the presence of infectious virus. The cell-based reporter assay can also be used as a potency assay. Also disclosed herein is a method for detecting infectious virus in a biological sample from a subject. The assay and methods disclosed herein can be conducted in a short period of time and are capable of accurately quantifying the amount of virus present in the sample.

In an aspect, the transgenic mammalian cells used in the assay and/or method are contacted with a sample comprising the virus or suspected of comprising the virus. In an aspect, the sample is taken from a batch of bulk virus before, during, or after storage of the bulk virus. The infectivity of a virus can potentially decrease during storage, and thus it is beneficial to have a quick and effective method of determining whether the expected amount of virus is present in a test sample after storage, i.e., a method to measure virus stability during storage over time. The assay results can be used to determine the fate of the bulk virus, for example, whether it is suitable for further use (e.g. manufacturing), or whether it should instead be modified or discarded. The assay can also be performed on a sample taken from a batch of vaccine comprising a live virus, such as an single cycle infectious virus, in which case the assay results can be used to determine the fate of the batch, e.g. whether the batch is suitable for release for use by healthcare professionals.

In an aspect, the sample is a biological sample from a subject. In an aspect, the virus is present in the biological sample or is suspected of being present in the biological sample. An assay capable of quickly and accurately testing (screening) a biological sample from a subject for the presence of infectious virus would be advantageous in providing a quick diagnosis and treatment of the subject. The biological sample can comprise, but is not limited to, serum, saliva, plasma, whole blood, nasopharyngeal swab, urine, stool, respiratory fluid, cerebrospinal fluid, or a combination thereof.

In an aspect, the contacting comprises infecting the transgenic mammalian cells with virus present in the sample. Following infection of the transgenic mammalian cells, the virus transactivates the virus promoter which induces expression of the reporter gene in the mammalian cells.

In an aspect, a cell based reporter assay method for measuring virus infectivity, comprises: providing transgenic mammalian cells comprising a heterologous nucleic acid stably integrated in a target locus on a chromosome of the genome of the mammalian cells, wherein the heterologous nucleic acid comprises a virus promoter operably linked to a reporter gene; contacting the transgenic mammalian cells with the sample, wherein infectious virus present in the sample transactivates the virus promoter which induces expression of the reporter gene in the mammalian cells; and quantifying the number of mammalian cells expressing protein encoded by the reporter gene to quantify the infectious virus.

In an aspect, a method of detecting infectious virus in a biological sample from a subject comprises: contacting the biological sample from the subject with transgenic mammalian cells comprising a heterologous nucleic acid stably integrated in a target locus on a chromosome of the genome of the mammalian cells, wherein the heterologous nucleic acid comprises a virus promoter operably linked to a reporter gene; contacting the transgenic mammalian cells with the biological sample, wherein infectious virus present in the sample transactivates the virus promoter which induces expression of the reporter gene in the mammalian cells; and quantifying the number of mammalian cells expressing protein encoded by the reporter gene to quantify the infectious virus.

In an aspect, the contacting comprises infecting the transgenic mammalian cells with the virus. In an aspect, the cell based reporter assay and/or method further comprises inducing expression of the reported gene in the transgenic mammalian cell. In an aspect, the transgenic mammalian cell is a Vero cell and the target locus comprises adeno-associated virus integration site 1 (AAVS1) on chromosome 6 of the Vero cell genome.

Disclosed herein also is a diagnostic method comprising the cell based reporter assay or the method of detecting infectious virus in a biological sample.

The present disclosure also provides transgenic mammalian cells that can be used to quantitate and characterize antigen-specific antibody-dependent cell-mediated cytotoxicity (ADCC) and/or antibody-dependent cell-mediated phagocytosis (ADCP).

In an aspect, the present disclosure provides a method of quantitating a rate or amount of ADCC in a population of cells, the method comprising: providing a plurality of transgenic mammalian cells comprising a heterologous nucleic acid stably integrated in a target locus on a chromosome of the transgenic mammalian cell genome, wherein the heterologous nucleic acid comprises a heterologous antigen gene configured for expression on the cell membrane of the transgenic mammalian cell and a gene encoding a fluorescent protein configured for expression in the cytoplasm of the transgenic mammalian cell; contacting the a plurality of transgenic mammalian cells with antibody and a population of immune cells; and quantitating at one or more time points the amount of the plurality of transgenic mammalian cells exhibiting fluorescence.

In an aspect, the present disclosure provides a method of quantitating a rate or amount of ADCP in a population of cells, the method comprising: providing a plurality of transgenic mammalian cells comprising a heterologous nucleic acid stably integrated in a target locus on a chromosome of the transgenic mammalian cell genome, wherein the heterologous nucleic acid comprises a heterologous antigen gene configured for expression on the cell membrane of the transgenic mammalian cell and a gene encoding a fluorescent protein configured for expression in the cytoplasm of the transgenic mammalian cell; contacting the a plurality of transgenic mammalian cells with antibody and a population of phagocytic cells; and quantitating at one or more time points the amount of phagocytic cells exhibiting fluorescence to quantitate the rate or amount of ADCP.

In an aspect, the transgenic mammalian cells designed for ADCC and/or ADCP methods are RMA cells. RMA cells are a T-cell lymphoma cell line from C57/B16 mice. Genetically modified RMA cells including the Bxb1 attB site (RMA-attB$_{Bxb1}$) can be cotransfected with mRNA encoding Bxb1 integrase and a heterologous nucleic acid including the attP site and gene encoding an antigen. The gene encoding the antigen is fused to a signal sequence and a transmembrane domain and operably linked to a constitutive promoter, and is expressed on a surface of the transfected cell. The heterologous nucleic acid further includes a reporter gene operably linked to a constitutive promoter such that the cell also expresses reporter gene in addition to the antigen.

The heterologous antigen gene encodes an antigen which induces an immune response specific for the target of interest e.g., virus, bacterium, parasite. As used herein an "antigen" refers to a polypeptide or protein capable of inducing an immune response, e.g., a humoral and/or cellular mediated response, to the target of interest in a subject.

The heterologous antigen gene can be from a virus, a bacterium, or a parasite. The virus can be a pathogenic virus, examples of which include adenovirus, cytomegalovirus (CMV), coxsackie virus, Crimean-Congo hemorrhagic fever virus, chikungunya virus, dengue virus, Dhori virus, Eastern equine encephalitis (EEE) virus, Ebola virus, Epstein Barr virus (EBV), Hanta virus, hepatitis viruses (e.g., hepatitis A, hepatitis B, hepatitis C, hepatitis D, hepatitis E), HSV-1, HSV-2, human immunodeficiency virus (HIV), human papilloma virus, human SARS corona virus, SARS CoV-2, human T lymphotropic virus (HTLV), influenza virus, Japanese encephalitis virus, Marburg virus, measles virus, mumps virus, poliovirus, Norwalk virus, smallpox, parvovirus, rabies virus, reovirus, rhinovirus, Rift Valley fever virus, rotavirus, rubella virus, severe fever with thrombocytopenia syndrome (SFTS) virus, respiratory syncytial virus (RSV), varicella zoster virus, Western equine encephalitis virus, West Nile virus, yellow fever virus, Zika virus, or a combination thereof.

The bacterium can be a pathogenic bacterium, examples of which include *Actinomyces* sp, *Bacillus* sp., *Bartonella* sp., *Bordatella* sp., *Borellia* sp., *Brucella* sp., *Campylobacter* sp., *Chlamydia* sp., *Clostridium* sp., *Corynebacterium* sp., *Coxiella* sp., *Enterobacter* sp., *Enterococcus* sp., *Escherichia* sp., *Francisella* sp, *Gardnerella* sp., *Haemophilus* sp., *Helicobacter* sp., *Klebsiella* sp., *Legionella* sp., *Leptospira* sp., *Listeria* sp., *Mycobacterium* sp., *Mycoplasma* sp., *Neisseria* sp., *Nocardia* sp., *Rickettsia* sp., *Pasteurella* sp., *Proteus* sp., *Pseudomonas* sp., *Salmonella* sp., *Serratia* sp., *Shigella* sp., *Staphylococcus* sp., *Streptococcus* sp., *Treponema* sp., *Vibrio* sp., *Yersinia* sp., or a combination thereof.

The parasite can be a pathogenic parasite, examples of which include *Acanthamoeba* spp., *Balamuthia* spp., *Babesia* sp., *Balantidium coli*, *Blastocystic* sp., *Cryptospiridium* sp., *Cyclospora cayetanensis*, *Entamoeba histolytica*, *Giardia lamblia*, *Isospora bello*, *Leishmania* sp., *Naegleria foweri*, *Plasmodium* sp., *Rhinosporidium seeberi*, *Sarcocystis* sp., *Toxoplasma gondii*, *Trichomonas* sp., *Trypanosoma* sp., or a combination thereof.

The transgenic cell lines are used as targets of ADCC or ADCP in combination with specific antibodies and specific effector cells. The antibodies and effector cells are obtained from individuals exposed to and/or infected with the microorganism (virus, bacteria, parasite) from which the antigen originates or from individuals vaccinated with a vaccine specific for the microorganism.

The amount of ADCC can be measured by microscope or by FACS by quantifying the loss of red fluorescence.

The amount of ADCP can be measured by quantifying the proportion of macrophages that are marked by the phagocytosis of the fluorescent transgenic cells.

The ADCC and ADCP methods disclosed herein simulate an infectious environment and are profoundly flexible, allowing for the use of polyclonal serum, different types of cell lines, and for example, different mouse strains.

This disclosure is further illustrated by the following examples, which are non-limiting.

Experimental Details

Verification of the AAVS1 Locus in Vero Cells

Based on sequence homology, the orthologous site of the adeno-associated virus integration site 1 (AAVS1) locus on human chromosome 19, resides on chromosome 6 in *Chlorocebus sebaeus*, the primate source of the Vero cell line. To verify the AAVS1 locus in Vero cells, genomic DNA from Vero cells (ATCC CCL-81) was extracted using DNAzol reagent following the manufacturer's recommendation. The purified genomic DNA was used as a template for PCR amplification using the primer pairs in Table 1.

TABLE 1

| Set | | Sequence | SEQ ID NO |
|---|---|---|---|
| 1 | Forward | AACTCGGAAACTGCCATAGCAGG | SEQ ID NO 4 |
|   | Reverse | GTTTCTTAGGGTGGTCTTCTCCG | SEQ ID NO 5 |
| 2 | Forward | GAAAGTGCAGGAGAGCCAGG | SEQ ID NO 6 |
|   | Reverse | CGATTAATATGGCTCTGGTTCTGG | SEQ ID NO 7 |
| 3 | Forward | CACAAAGGGAGTTTTCCACACGGAC | SEQ ID NO 8 |
|   | Reverse | CACGACCTGCTGGTTCTCAGTGG | SEQ ID NO 9 |

Sanger sequencing of the purified PCR products verified that the regions amplified were 90% identical to the human AAVS1 locus. A 4086 bp consensus sequence having the sequence of SEQ ID NO 22, was generated and designated Vero AAVS1, corresponding to coordinates 47705457 to 47709543 on chromosome 6 (NCBI Reference Sequence: NC_023647.1) of the Vero cells.

Design of Cas9 Guide RNA to Target Vero AAVS1 Locus

The identification of putative guide RNA (gRNA) was conducted using the Chop Chop server (https://chopchop.cbu.uib.no/_) by uploading the Vero AAVS1 site obtained through Sanger sequencing and running an algorithmic search. Five different synthetic single guide RNAs (sgRNA) were generated to create double stranded DNA breaks between positions 1529 and 1530, positions 2408 and 2409, positions 2155 and 2156, positions 2037 and 2038, and positions 1416 and 1417 of the AAVS1 sequence. The gRNA sequences were synthesized by Integrated DNA Technologies (IDT DNA), and included modifications to increase the gRNA stability. The top 3 candidate synthetic guide RNAs, specifically sgRNAs, were chosen and submitted for chemical synthesis at IDT DNA which included modifications to increase the RNA stability. FIG. 2 is a schematic illustration of the Vero AAVS1 site and the location of the top three candidate single gRNAs: (1) a gRNA which creates a double stranded break between position 1529 and 1530 of the Vero AAVS1 sequence, (2) a gRNA which creates a double stranded break between position 2155 and 2156 of the Vero AAVS1 sequence, and (3) a gRNA which creates a double stranded break between position 2408 and 2409 of the Vero AAVS1 sequence.

The sequence of the synthetic gRNA that creates a double stranded break between position 1529 and 1530 of the Vero AAVS1 site has the sequence of SEQ ID NO 10. The underlined portion of SEQ ID NO 10 represents the 20 nucleotide crRNA region.

(SEQ ID No. 10)
mA*mG*mA* <u>rGrGrA rArCrA rArUrA rCrArA rArUrU rCr-</u>
<u>GrG</u> rUrUrU rUrArG rArGrC rUrArG rArArA rUrArG rCrArA rGrUrU ArArA rArUrA rArGrG rCrUrA rGrUrC rCrGrU rUrArU rCrArA rCrUrU rGrArA rArArA rGrUrG rGrCrA rCrCrG rArGrU rCrGrG rUrGrC mU*mU*mU* rU

The sequence of the synthetic gRNA that creates a double stranded break between positions 2155 and 2156 of the Vero AAVS1 has the sequence of SEQ ID NO 20. The underlined portion of SEQ ID NO 20 represents the 20 nucleotide crRNA region.

(SEQ ID NO 20)
mC*mC*mU* <u>rGrCrA rArGrA rUrGrC rCrGrU rGrArC rAr-</u>
<u>GrG</u> rUrUrU rUrArG rArGrC rUrArG rArArA rUrArG rCrArA rGrUrU rArArA rArUrA rArGrG rCrUrA rGrUrC rCrGrU rUrArU rCrArA rCrUrU rGrArA rArArA rGrUrG rGrCrA rCrCrG rArGrU rCrGrG rUrGrC mU*mU*mU* rU

The sequence of the synthetic gRNA that creates a double stranded break between positions 2408 and 2409 of the Vero AAVS1 has the sequence of SEQ ID NO 21. The underlined portion of SEQ ID NO 21 represents the 20 nucleotide crRNA region.

(SEQ ID NO 21)
mC*mC*mA* <u>rCrCrC rUrArA rGrArA rArCrG rAr-</u>
<u>GrA rGrArG</u> rUrUrU rUrArG rArGrC rUrArG rArArA rUrArG rCrArA rGrUrU rArArA rArUrA rArGrG rCrUrA rGrUrC rCrGrU rUrArU rCrArA rCrUrU rGrArA rArArA rGrUrG rGrCrA rCrCrG rArGrU rCrGrG rUrGrC mU*mU*mU* rU

Design of Single-Stranded DNA Containing attB Flanked by Vero Homology Sequences A single stranded DNA fragment was chemically synthesized by IDT DNA which contains the 38 nucleotide attB sequence flanked by 40 nucleotides corresponding to Vero AAVS1 sequence upstream of position 1529 and 40 nucleotides corresponding to Vero AAVS1 sequence downstream of position 1529. The sequence is shown below:

(SEQ ID NO 1)
TCTCACAGGGAAAACTGATGCAC<u>AGAGGAACAATACAAAT</u>GGCTTGTCGAC

GACGGCGGTCTCCGTCGTCAGGATCAT<u>TC</u>GGGGCTAGAAAGGTGAAGACC

CAAAATTAGAACTCAGG

In SEQ ID NO. 1, the underlined nucleotides indicate the sequence corresponding to the crRNA while the bold nucleotides indicate the attB sequence.

Co-transfection of Cas9-gRNA Complexes and Single-Stranded Oligonucleotide

Cas9-gRNA complexes were formed by mixing 4 microliters (µl) of Cas9 protein (20 µM in NEB Buffer 3, 80 pmol; New England Biolabs, Ipswich, MA) with 1 µl of the synthetic gRNA (100 µM in Tris-EDTA, 100 pmol, IDT, Coralville, IA) targeting the Vero AAVS1 site. The mixture was incubated for 20 minutes at room temperature. At the end of the incubation, 1 µl of single-stranded DNA (100 µM in Tris-EDTA, 100 pmol, IDT, Coralville, IA) containing the 38-bp attB sequence flanked by 40-bp of Vero homologous sequences was added (SEQ ID NO. 1). To this mixture was added 20 µl of a Vero cell suspension ($2.5 \times 10^5$ cells total, in Lonza Buffer SF). This mixture was transferred to a single chamber of a 16-well Nucleocuvette strip and the cells were subjected to nucleofection (electroporation-based transfection) using the Nucleofector X unit (Lonza, Basel, Switzerland) with program DN-100.

After electroporation, the cell suspension was transferred to two wells of a 12-well plate containing 1 milliliter (ml) of 5% FBS/DMEM and incubated at 37° C. in 5% $CO_2$. The cells were grown to confluence (1 week), trypsinized and seeded into 96-well plates for clonal selection by limiting dilution.

Screening Cells for the Presence of attB Insertion.

Confirmation of homologous recombination was confirmed by PCR. A portion of the Vero attB cells were lysed and genomic DNA was extracted. Specifically, the 96-well plates containing Vero transfectants were replica plated into two 96-well plates. One plate was used to continue culturing the cells, while cells in the second plate were lysed by the addition of 50 µl of 1 µg/ml of Primase in Tris-HCl (pH 8), to each well. After incubating for 5 mins at 37° C., the cells were detached and transferred to a 96-well PCR plate. The plate was sealed and heated to 95° C. for 15 mins and cooled. The genomic DNA was used as a template for PCR amplification using a primer pair that bound to the attB site (primer 1529attB_F: SEQ ID NO 25, Table 2) and position 1529 (primer 1529attB R: SEQ ID NO 26, Table 2) of the Vero AAVS1 site. The PCR products were analyzed directly by agarose gel electrophoresis.

Figure 3:
FIG. 3 is a schematic illustration of the Vero AAVS1 site with Bxb1 attB (SEQ ID NO 2) inserted into position 1529.
Figure 4A:
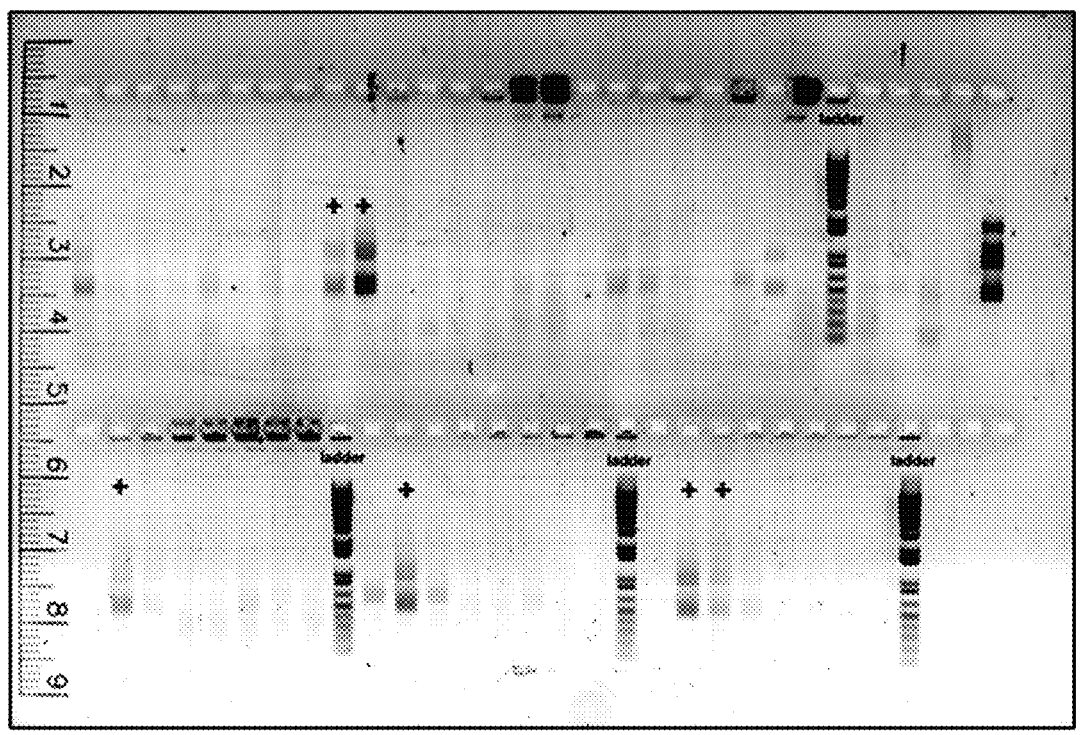
FIG. 4A is an agarose gel showing PCR results identifying possible attB-containing Vero cell clones, which are denoted by a + sign.
Figure 4B:
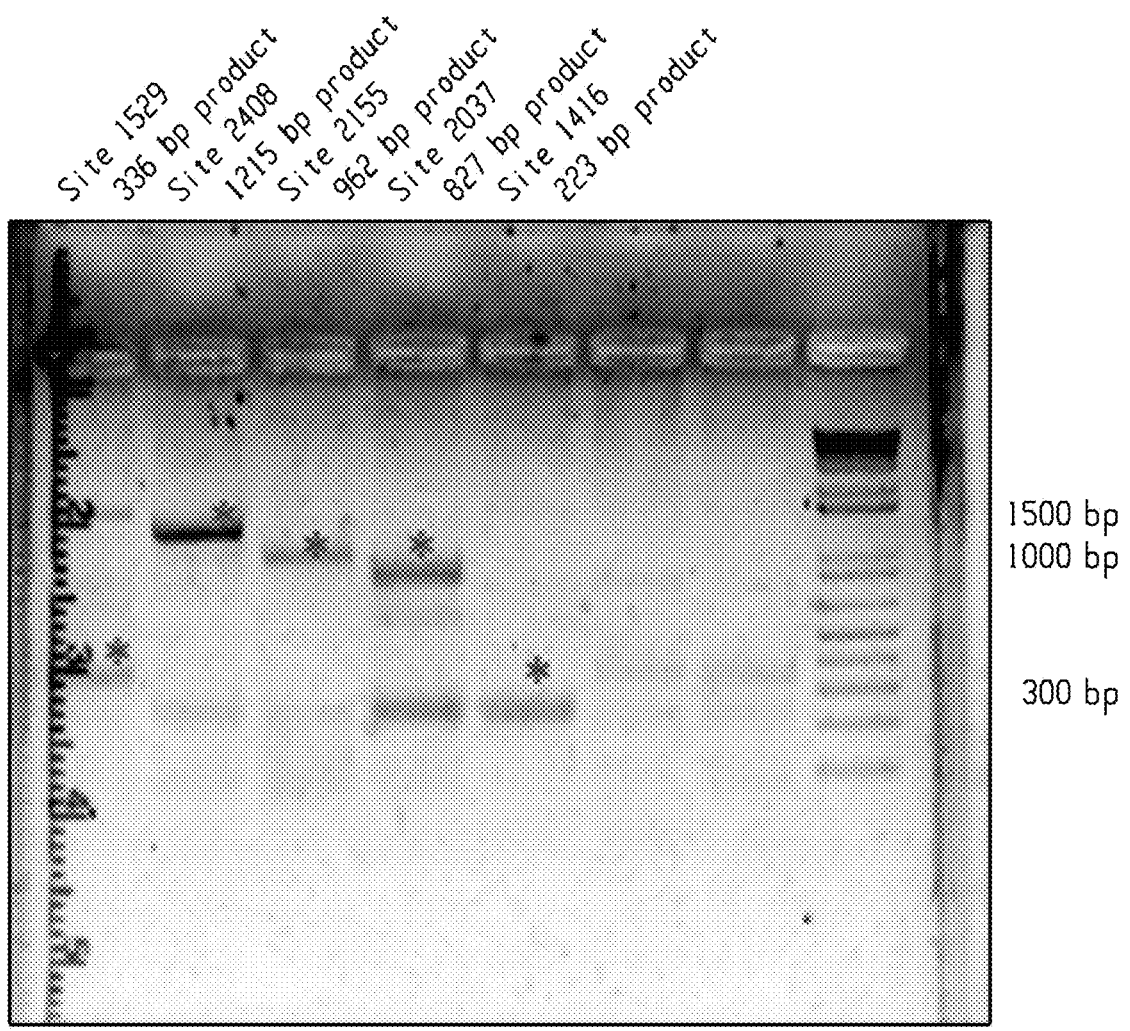
FIG. 4B shows the PCR results verifying the site-specific insertion of Bxb1 attB in chromosome 6 of the cloned Vero:attB cells.
Figure 5:
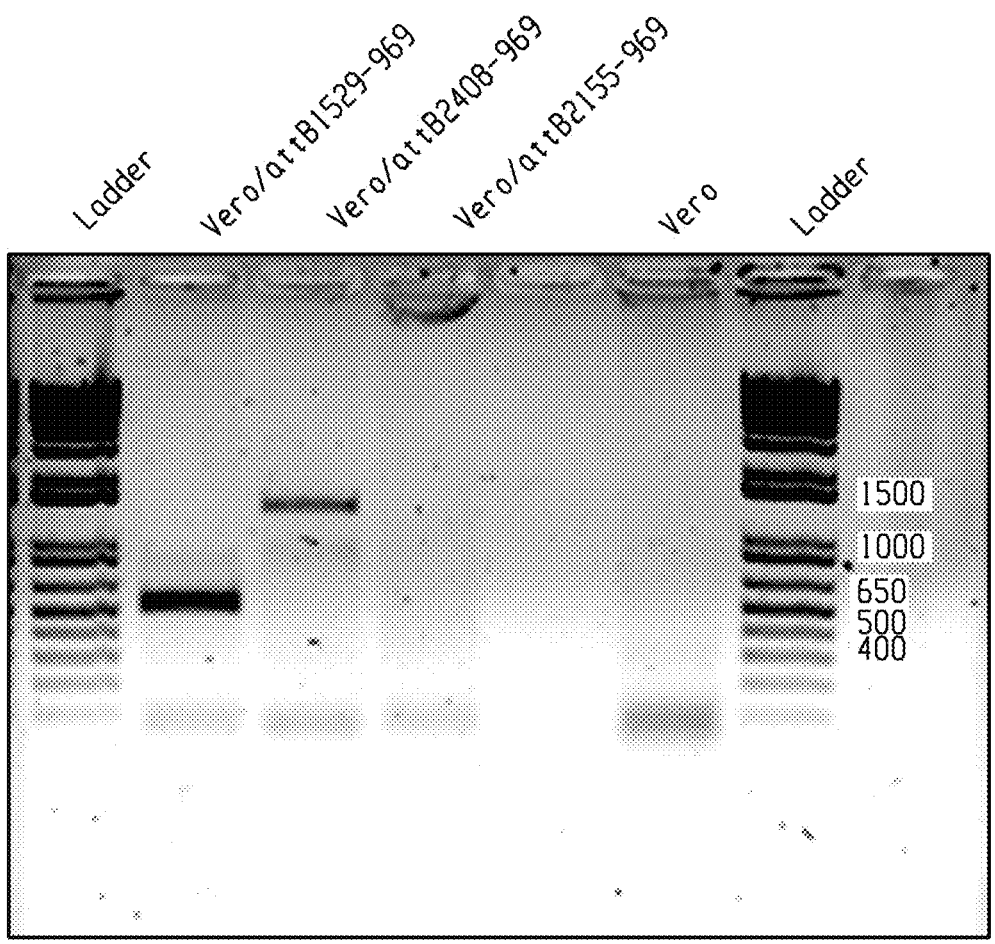
FIG. 5 shows the PCR results verifying the site-specific insertion of the HSV gene-containing plasmid in chromosome 6 of Vero:attB cells.

FIG. 3 is a schematic illustration of the Vero AAVS1 site with the attB inserted into position 1529. FIG. 4A shows the results identifying possible attB-containing Vero cell clones (lanes denoted by + sign). FIG. 4B also shows PCR results verifying the site-specific insertion of Bxb1 attB in chromosome 6 of Vero:attB cells.

Sanger sequencing to confirm identification of Vero cells containing attB (VerB cells)

Candidate clones from the initial screen for Vero/attB were expanded into T-25 flasks. For a 2nd round of screening, Sanger sequencing was performed on PCR products generated by amplifying the region surrounding the putative attB insertion site (position 1529 in the Vero AAVS numbering system). Approximately $1 \times 10^6$ cells from each clone were lysed using a Monarch® Genomic DNA purification kit (NEB cat T3010L, NEB, Ipswich, MA). The purified template was used for PCR using NEBNext® Ultra™ II Q5 Master Mix (cat #NEB M0544, NEB, Ipswich, MA). The primers used for sequencing were: forward primer 1201F (AATCTGAGCGCCTCTCCTGG, SEQ ID NO 27) and reverse primer 2471R (CCCCCATGCCATCTTCACTC, SEQ ID NO 28). Sanger analysis confirmed the successful insertion of attB into clone 3C, and this new Vero::attB cell line was designated as cell line $VerB_{1529}\alpha$.

Construction of hisD-attP Cosmid Containing HSV-1 Genes US4-US7 (pBRL969)

The 4.3 kb HSV1 BamHI J fragment was amplified from VD60 cells (Ligas, et al, 1988, J. Virol., 62, 1486-1494) using the primers, CCGCTGTTTCAACAGAAATGACC (SEQ ID NO 11) and CCAACTCAGTGACTGCGGTCG (SEQ ID NO 12) and cloned in pCR4blunt Topo vector. The fragment includes the Us4, Us5, Us6, and Us7 genes from HSV-1 encoding the glycoproteins G, J, D, and I, respectively. The fragment was isolated by EcoRI digestion and blunted by DNA Polymerase I, Large (Klenow) and cloned in the hisD vector pYUB2941 at the Bst1107I site resulting in pYUB2942. In order to use hisD gene as a marker in *E. coli*, the EM7 promoter was amplified from the plasmid ptwB using the primers ptwB_5996 and ptwB_6082, having the sequences shown in Table 2.

Figure 8:
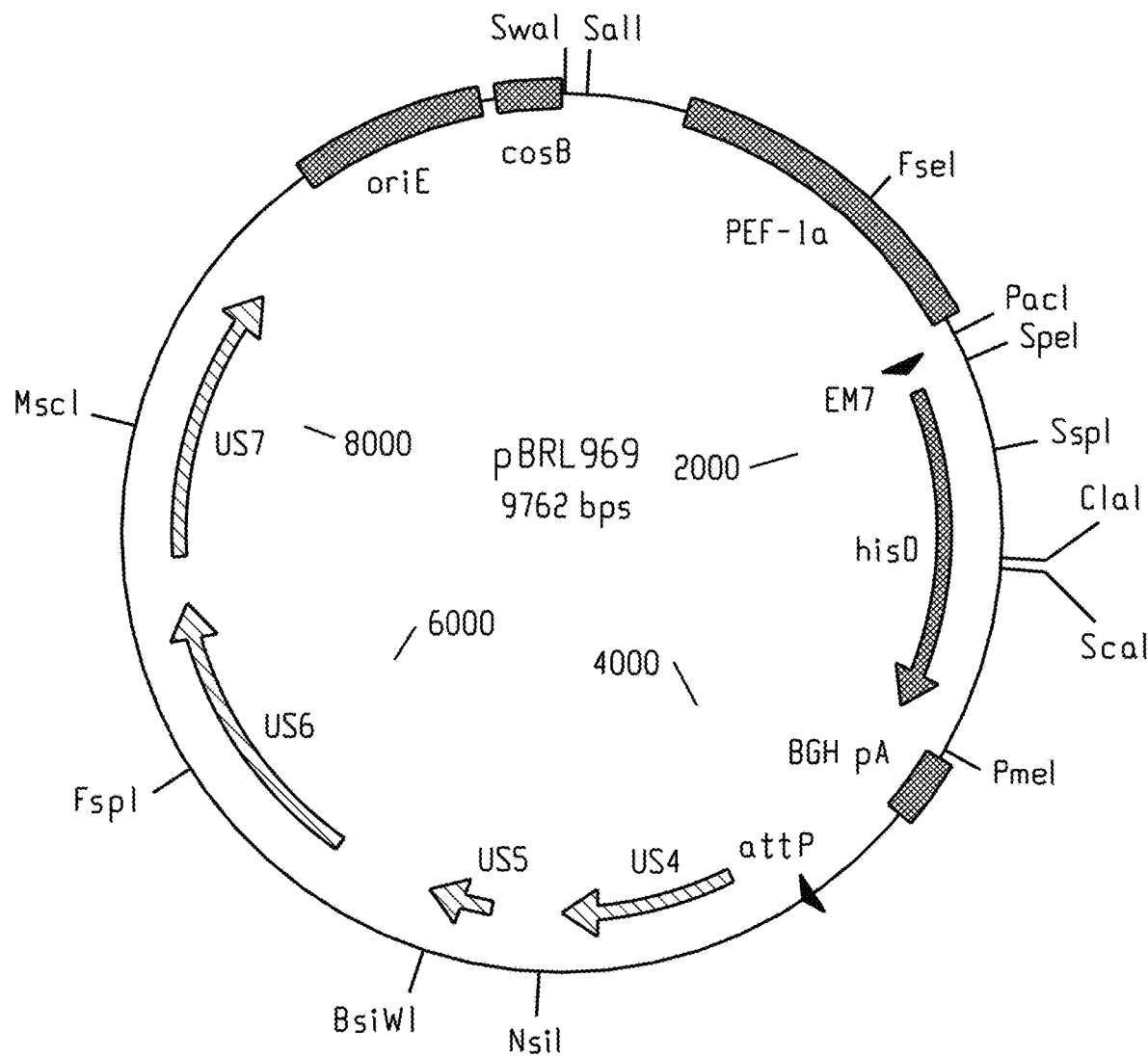
FIG. 8 is the HSV-1 containing plasmid (pBRL969) consisting of a 4 kB DNA fragment that is PCR amplified from VD60 and inserted into a plasmid which has a COLE1 origin of replication, a 38 base pair DNA sequence including the attP locus from mycobacteriophage Bxb1, a 200 bp sequence encoding the KOS site of bacteriophage lambda, and a DNA fragment encoding the *Salmonella typhimurium* gene encoding hisD which has a prokaryotic promoter and a eukaryotic promoter.
Figure 9:
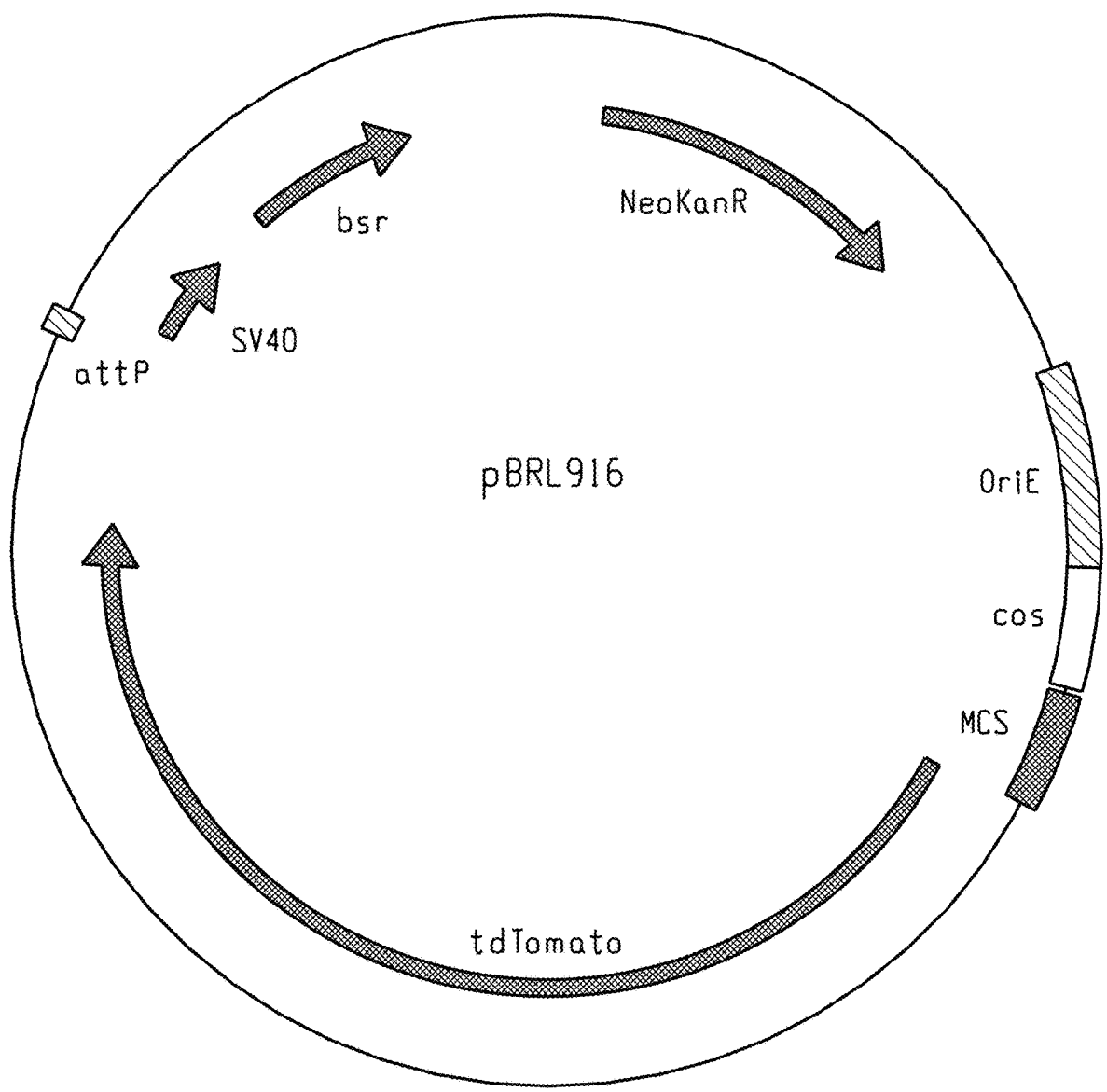
FIG. 9 is a map of the plasmid designated pBRL916.

The resulting product was cloned into the Acc65I site of pYUB2942 resulting in pYUB2943. The Bxb1 attP was amplified from pBRL834 with primers pBRL834_352-attP_F (forward) and pBRL834_attP_R (reverse) having the sequences shown in Table 2 and cloned in the PsiI site of pYUB2943 creating pBRL961. The hisD cosmid without the antibiotic marker, pBRL969 (FIG. 8), was constructed by amplifying lambda cos from pYUB328 by using the primers pYUB328-cosBF (forward) and pYUB328-cosBR (reverse)(sequences shown in Table 2), and then replacing the BspHI fragment of pBRL961 with this fragment in *E. coli* strain UTH4314 (F⁻hisD4314, thyA321, deo-71).

TABLE 2

| Primer | Sequence |
| --- | --- |
| ptwB_5996 | GCGGCGTGCGGTACCCATGTTCTTAATTAAATTT TTC (SEQ ID NO 13) |
| ptwB_6082 | GCGCTGGCGGTACCCCTATAGTGAGTCGTATTA TAC (SEQ ID NO 14) |
| pBRL834_352-attP_F | GCGCGCGGCTTATAAGGTTTGTCTGGTCAACCA (SEQ ID NO 15) |
| pBRL834_attP_R | GCGCGCGGCTTATAAGGTTTGTACCGTACACCAC (SEQ ID NO 16) |
| pYUB328-cosBF | GCGCGTTAGTCATGAGCTAGCCGATCCGCCTTGT TACGGGG (SEQ ID NO 17) |
| pYUB328-cosBR | GCGCGCGTTCGTCATGAATTTAAATACGTGTCTA GATACGTCTGC (SEQ ID NO 18) |
| 1231F | CTTGCCAGGGACTCAAACCC (SEQ ID NO 23) |
| attR | ATGATCCTGACGACGGAGAC (SEQ ID NO 24) |

TABLE 2-continued

| Primer | Sequence |
|---|---|
| 1529attB_F | GTCGACGACGGCGGTCTC (SEQ ID NO 25) |
| 1529attB_R | GACCGCTTCTATTCCCAGG (SEQ ID NO 26) |

Synthesis of mRNA Encoding Bxb1

The pCAGGS plasmid containing the HA-tagged BxB1 gene with the SV40 nuclear localization sequence downstream of a T7 promoter (pCAGGS/HA-NLS BxB1) was used as a template for in vitro mRNA synthesis using the CellScript T7 mScript mRNA production kit (Madison, WI). The in vitro transcribed mRNA was purified using a Stratagene Absolutely RNA miniprep kit (La Jolla, CA).

Integration of pBRL969 into Vero::attB Cells

Vero:attB cells were subjected to recombination with a plasmid containing the matching Bxb1 attP site by cotransfecting mRNA encoding the BxB1 integrase and the plasmid pBRL969. A transfection complex was formed by mixing 2 µg of plasmid pBRL969, 1 µg of mRNA encoding the Bxb1 integrase, and 2×10⁶ Vero:attB cells in 100 µl of Lonza SF buffer. This mixture was transferred to a 100 ul Nucleofector cuvette and electroporated using the Nucleofector X unit with program DN-100.

After electroporation, the cell suspension was transferred to a 150-mm diameter tissue culture dish containing 20 ml of 5% FBS/DMEM. After 3 days, the medium was removed and replaced with 20 ml of 5% FBS/-histidine DMEM supplemented with 2 mM of histidinol. After 1 week in culture, individual cells (clones) were selected using cloning rings. Individual clones were transferred to 12-well plates and expanded. Non-selected cells were pooled and lysed for genomic DNA analysis. The genomic DNA was used as a template for PCR amplification using a primer pair that bound to the HSV gG gene (primer gG) and position 2471 of the Vero AAVS1 site. FIG. 4B shows the PCR results verifying the site-specific insertion of the HSV gene-containing plasmid in chromosome 6 of Vero:attB cells. The insertion frequency of Bxb1 integration of the plasmid DNA is about 10-20%. The nucleic acid integrated into the Vero:attB cells has a sequence corresponding to SEQ ID NO 19.

Figure 6:
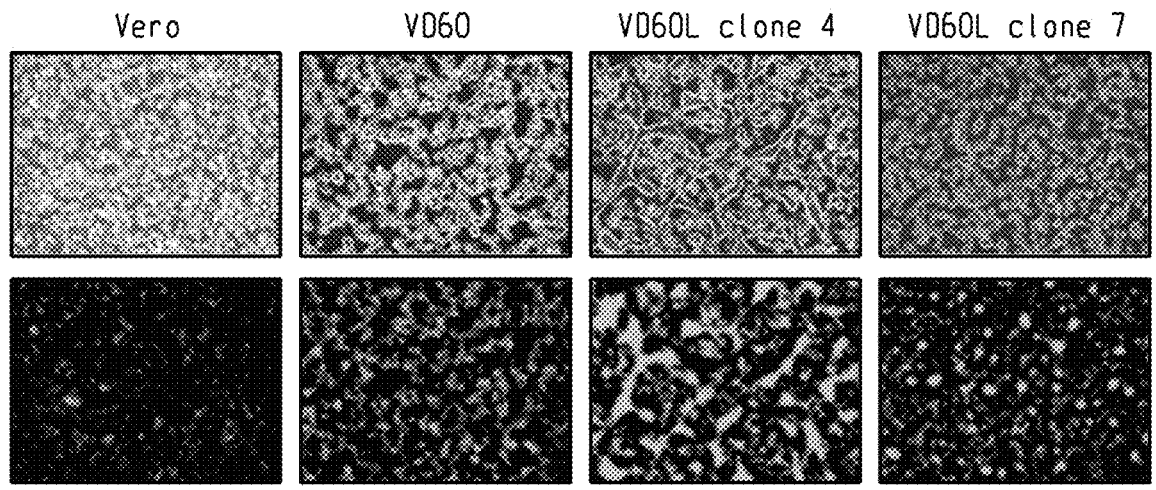
FIG. 6 shows the results of a plaque assay testing the ability of VD60L clones to support propagation of ΔgD-2:: RFP and includes photographs showing expression of RFP in VD60 cells, VD60L cells, and Vero cells.
Figure 7:
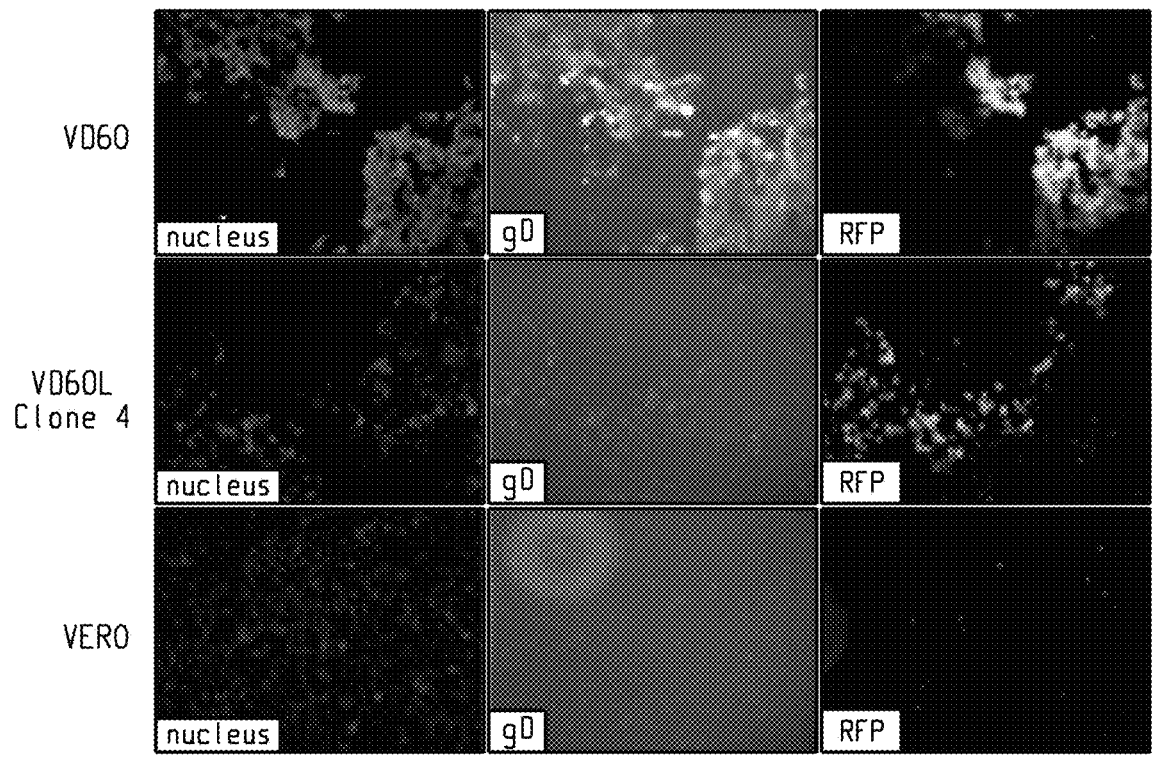
FIG. 7 is photographs showing expression of gD and RFP in VD60 cells, VD60L cells, and Vero cells following infection with the ΔgD-2::RFP recombinant.

The clones were tested for their ability to support propagation of ΔgD-2 and their infectious titer determined in a plaque assay. Plated cells were infected at an MOI of 0.1 with ΔgD-2 virus expressing RFP and harvested 24 hours post infection. Virus was extracted from infected cells by sonication. After centrifugation to remove cellular debris, the supernatant was assayed to quantify the amount of virus. The results of the plaque assay are shown in FIG. 6 and in Table 3 below.

TABLE 3

| Cells | PFU/ml |
|---|---|
| VD60 | $3.6 \times 10^5$ |
| VD60L, clone 4 | $5.33 \times 10^4$ |
| VD60L, clone 7 | $2.67 \times 10^4$ |

Testing of VD60L Cells for Expression of gD Protein and Viral Propagation

Clones from screen were tested for their ability to express gD after infection with ΔgD-2::RFP and for their ability to support propagation of ΔgD-2::RFP. The ΔgD-2::RFP is an engineered HSV-2 virus in which the gD gene (ΔgD-2) is deleted and replaced with a gene that strongly expresses the red fluorescent protein (RFP). The ΔgD-2::RFP recombinant is made from a ΔgD-2 that previously showed protection against infection in mice.

VD60 and VD60L cells were infected with the ΔgD-2::RFP recombinant and expression and expression of gD and RFP in the cells was evaluated. Plated cells were infected at an MOI of 0.01 and fixed in paraformaldehyde 2 days after infection. The expression of glycoprotein gD was observed by immunofluorescence staining using a mouse antibody raised against gD, and a fluorescent secondary antibody against mouse IgG. The results for Clone 4 are shown in FIG. 7. FIG. 6 shows that infection with ΔgD-2::RFP at an MOI of 0.1 results in virus propagation and CPE in VD60 and VD60L clones.

We also propose the use of alternative HSV-1 sequences to complement ΔgD-2. For example:

A. A single copy of gD-1 from KOS strain or any other HSV-1 strain;

B. The open reading from gD-1 from KOS strain or any other HSV-1 strain, fused to an exogenous cellular promoter such as EF-1α;

C. Multiple copies of genes from A or B above;

D. Multiple copies of the genes encoding glycoproteins G, J, D and I from KOS or any other HSV-1 strain.

The above experiments illustrate the production of genetically modified Vero cells which contain the attB sequence integrated in a target locus on chromosome 6 (Vero:attB). The attB site was introduced into multiple specific locations in the AAVS1 site of the Vero cell line using CRISPR-Cas9 system, but is not limited thereto, and other sites within AAVS1 or other loci within the genome can also be targeted. Vero attB cell lines will provide a highly efficient system for generating complementing and reporter cell lines for both production of vaccine viruses and assay development.

Also disclosed herein are genetically modified Vero cells in which HSV-1 glycoprotein D is inserted in the target locus on chromosome 6 of the Vero cell genomic DNA. As a proof of principle, a new plasmid including the HSV-1 glycoprotein D gene and devoid of an antibiotic resistance marker and an SV40 sequence was integrated into Vero/attB cells to produce VD60L cells expressing glycoprotein D. The VD60L cells were demonstrated to complement ΔgD-2. Moreover, a method of expressing the Bxb1 integrase by transfecting a mRNA encoding the integrase with a nuclear localization sequence was also developed. This method mediates efficient integration of attP plasmids into the attB site.

FIG. 1 illustrates a summary of the method of preparing the Vero:attB cell line and the VD60L cell line.

HSV-2 Inducible Reporter Cell Line to Rapidly Assess the Quantity of Infectious Attenuated Virus Particles in Vaccine Preparation We propose to develop a transgenic Vero cell line which contains a reporter gene (e.g., RFP, GFP, nanoLuc) fused to an HSV promoter, and which will be expressed upon infection of the cell with the ΔgD-2 virus. The transgenic Vero cell line will be derived from the Vero attB cell line disclosed herein. An exemplary plasmid construct (pBRL916) for preparing the transgenic cell line is shown in FIG. 9. The plasmid pBRL916 includes: a gene for blasticidin resistance expressed from an SV-40 promoter as a selection marker in eukaryotic cells, the Bxb1 attP site that allows integration into the attB site in the Vero::attB cells, a bacteriophage lambda cos cite that allows for multimerization, and a red fluorescent protein gene expressed via an experimentally defined HSV-2 promoter which is typically off, but is activated when the Vero cell is infected with the ΔgD-2 virus. Promoters from the following HSV-2 genes will be cloned into pBRL916 and assessed for optimal activity within 1-2 hours post infection with ΔgD-2 virus. The following HSV-2 promoters will be tested:

| |
|---|
| ICP0 |
| ICP4 |
| ICP27 |
| ICP8 |
| TK |
| VP5 |

In order to determine the optimal promoter-reporter construct, each of the promoters will be cloned into the pBRL916 vector and cotransfected into Vero::attB cells with mRNA encoding the Bxb1 integrase, and selected with blasticidin. The resulting cell lines will be infected with ΔgD-2, and expression of the reporter will be analyzed by FACS or a 96-well plate luminometer. The optimal time post-infection for measuring reporter expression will be determined. A standard curve will be derived that will correlate reporter activity with plaque-forming units, and thus the titer of the vaccines can be assessed in a few hours instead of days.

Antigen Target Cell Line to Quantitate and Characterize Antibody-Dependent Cell-Mediated Cytotoxicity (ADCC) and/or Antibody-Dependent Cell-Mediated Phagocytosis (ADCP)

The levels of Fc-receptor-activating antibodies produced by an individual in response to a viral infection or vaccination with a viral vaccine, and specifically FcγRIV activating antibodies, is currently measured using the Promega Mouse FcγRIV ADCC Bioassay. The assay utilizes a Jurkat T-Cell line in which a nanoLuc gene is fused to a STAT promoter. While the assay has been useful for quantifying FcγRIV activating antibody levels, it does not assess the type of immune cells mediating the killing of infected cells. In addition, different immune effectors may play different roles in ADCC immunity. Therefore, we propose to develop cell lines that can both quantitate and discriminate between ADCC or ADCP.

To achieve this, we plan to use the RMA cell line, which is a T-cell lymphoma from C57/B16 mice. We will introduce the attB sequence into a non-essential region of the mouse chromosome in the RMA cells. The resulting RMA-attB$_{Bxb1}$ cell line will be cotransfected with a plasmid engineered to express a target antigen on the surface of the cell and mRNA encoding the Bxb1 integrase. The resulting transgenic RMA cells will express the antigen on the surface of the cells. In addition to expressing the antigen target on the cell surface, the cells also constitutively express red fluorescence cytoplasmically. For example, a reporter gene (e.g., RFP gene) will be fused to the highly efficient promoter of the EF1α (Elongation Factor 1α) gene and its expression is easily detected using a fluorescent microscope or by FACS.

Figure 10:
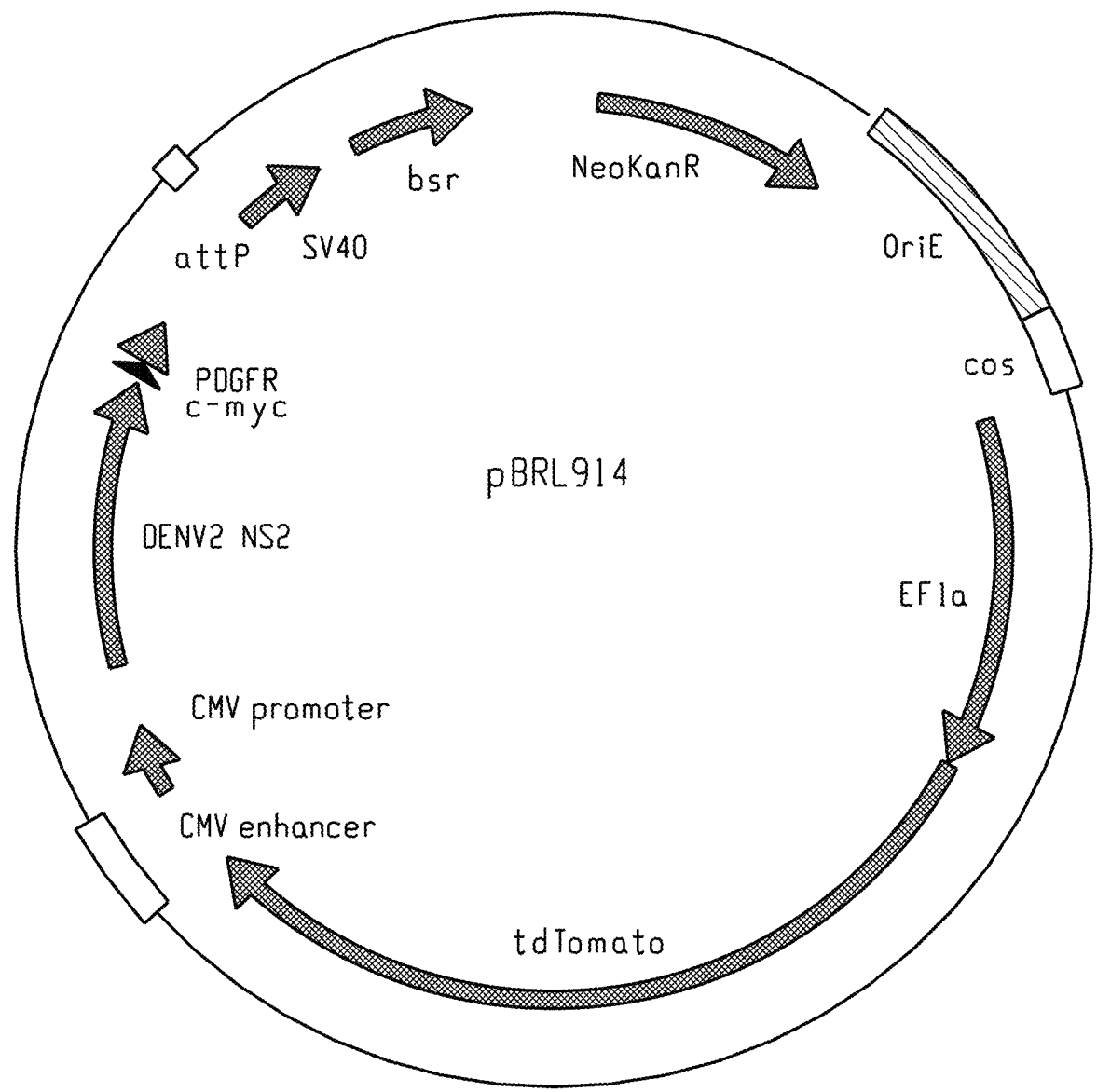
FIG. 10 is a map of the plasmid designated pBRL914.
Figure 11:
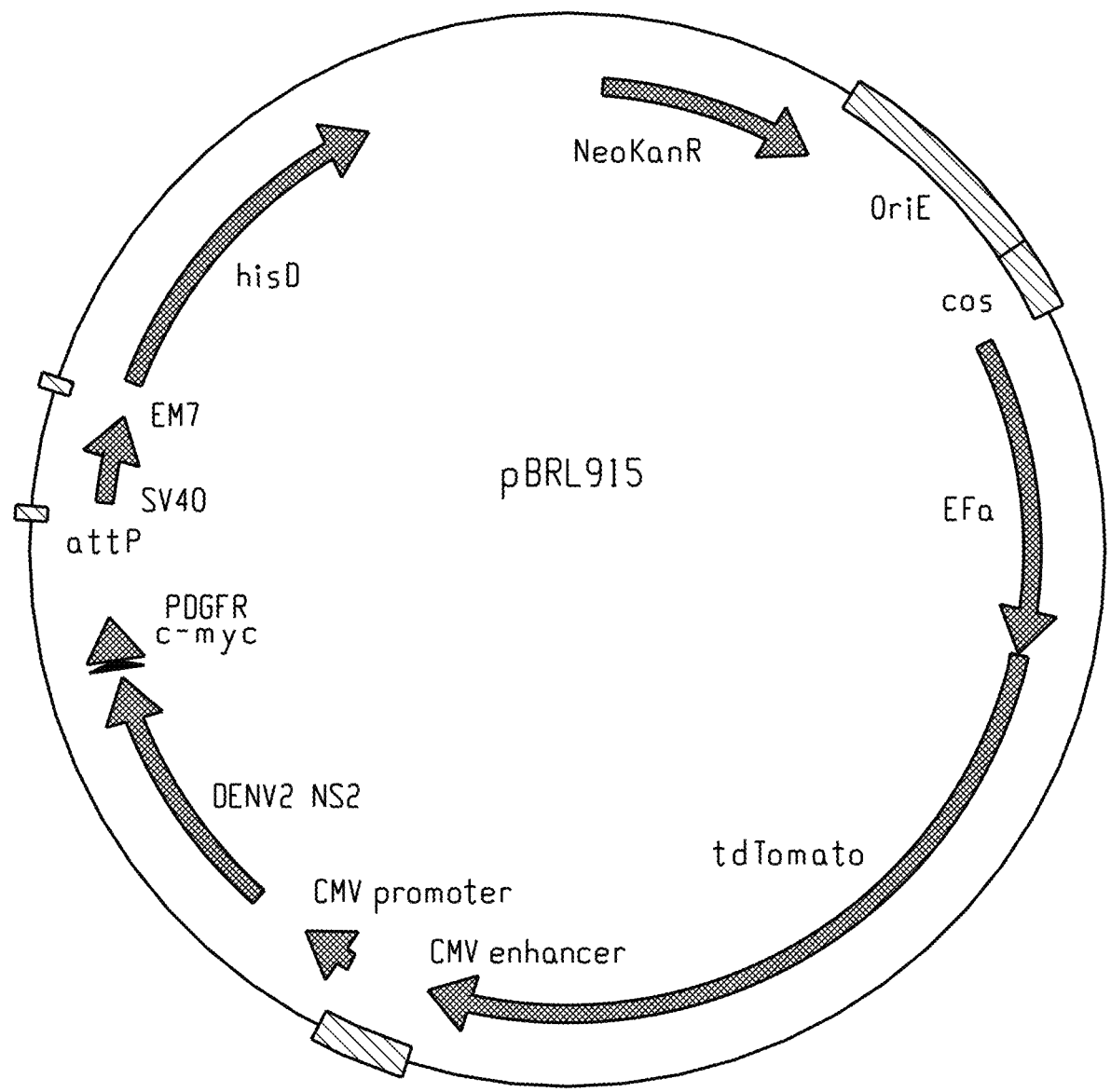
FIG. 11 is a map of the plasmid designated pBRL915.

Exemplary plasmid constructs pBRL914 and pBRL915 are shown in FIG. 10 and FIG. 11, respectively.

pBRL914 (FIG. 10) is designed to express the NS1 protein from dengue virus strain DENV2 on the surface of infected cells. The gene encoding the NS1 protein is fused to a signal sequence from the immunoglobulin kappa and a transmembrane domain from the platelet-derived growth factor receptor (PDGFR). pBLR914 also encodes blasticidin resistance as a selection marker in eukaryotic cells expressed from an SV-40 promoter, red fluorescent protein (RFP) expressed via the EF-1α promoter, the attP site from Bxb1 that allows integration into the attB site in the RMA-attB$_{Bxb1}$ cells, and bacteriophage lambda cos that allows for multimerization.

pBRL915 (FIG. 11) is substantially the same as pBRL914 except the blasticidin resistance gene has been replaced with the hisD gene from *Salmonella typhimurium* fused to complement hisD mutants of *E. coli* and confers resistance to histidinol in eukaryotic cells. This resistance eliminates the need for an antibiotic resistance selection.

The engineered cell lines will be used as targets of ADCC or ADCP in combination with specific antibodies and specific effector cells. The antibodies and effector cells will be obtained from individuals exposed to and/or infected with the microorganism (virus, bacteria, parasite) from which the antigen originates or from individuals vaccinated with a vaccine. ADCC will be measured microscopically or by FACS by quantifying the loss of red fluorescence. ADCP will be measured by the proportion of macrophages that are marked by the phagocytosis of the fluorescent transgenic cells.

The compositions, methods, and articles can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combinations" is inclusive of blends, mixtures, alloys, reaction products, and the like. The terms "first," "second," and the like, do not denote any order, quantity, or importance, but rather are used to distinguish one element from another. The terms "a" and "an" and "the" do not denote a limitation of quantity and are to be construed to cover both the singular and the plural, unless otherwise indicated herein or clearly contradicted by context. "Or" means "and/or" unless clearly stated otherwise. Reference throughout the specification to "some embodiments", "an embodiment", and so forth, means that a particular element described in connection with the embodiment is included in at least one embodiment described herein, and may or may not be present in other embodiments. In addition, it is to be understood that the described elements may be combined in any suitable manner in the various embodiments. A "combination thereof" is open and includes any combination comprising at least one of the listed components or properties optionally together with a like or equivalent component or property not listed.

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

While embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A genetically modified mammalian cell comprising a recombination sequence inserted in a target locus on a chromosome of the Vero cell genome, wherein the recombination sequence comprises a Bxb1 attB sequence from *Mycobacterium smegmatis* wherein the mammalian cell is a Vero cell and the target locus comprises adeno-associated virus integration site 1 (AAVS1) on chromosome 6 of the Vero cell genome, wherein the AAVS1 locus comprising the recombination sequence has the 4 kilobase sequence of SEQ ID NO:22.

2. The genetically modified mammalian cell of claim 1, wherein the attB site is inserted between positions 1529 and 1530 of the AAVS1 locus, between positions 2155 and 2156 of the AAVS1 locus, between positions 2408 and 2409 of the AAVS1 locus, or a combination thereof.

3. The genetically modified mammalian cell of claim 1, wherein the attB sequence has the sequence of

GGCTTGTCGACGACGGCGGTCTCCGTCGTCAGGATCAT. (SEQ ID NO 2)

4. A cell line comprising the genetically modified mammalian cell of claim 1.

5. A method of producing a genetically modified mammalian cell of claim 1, the modified mammalian cell comprising a recombination sequence inserted in a target locus on a chromosome of the Vero cell genome, wherein the recombination sequence comprises Bxb1_attB sequence from *Mycobacterium smegmatis*, the method comprising:
providing a complex comprising
a guide RNA comprising an oligonucleotide sequence that hybridizes with a target site on the target locus, and
a Cas9 endonuclease;
providing a single stranded DNA sequence comprising the attB sequence; and
introducing the complex and the single stranded DNA sequence into a Vero cell to obtain a genetically modified Vero cell comprising the Bxb1 attB sequence inserted in the target locus.

6. The method of claim 5, wherein the Bxb1 attB sequence is inserted between positions 1529 and 1530 of the AAVS1 locus, between positions 2155 and 2156 of the AAVS1 locus, between positions 2408 and 2409 of the AAVS1 locus, or a combination thereof.

7. The method of claim 5, wherein the Cas9 endonuclease catalyzes a DNA break at the target site upon hybridization of the target site with the gRNA.

8. The method of claim 5, wherein the single stranded DNA sequence has the sequence of SEQ ID NO 1.

9. The method of claim 5, wherein the guide RNA has a sequence of SEQ ID NO 10, SEQ ID NO 20, SEQ ID NO 21, or a combination thereof.

10. A transgenic mammalian cell comprising a heterologous nucleic acid stably integrated in a target locus on a chromosome of the genome of the genetically modified mammalian cell of claim 1, wherein the heterologous nucleic acid comprises a heterologous gene configured for expression by the transgenic mammalian cell.

11. The transgenic mammalian cell of claim 10, wherein the heterologous nucleic acid is inserted between positions 1529 and 1530 of the AAVS1 locus, between positions 2155 and 2156 of the AAVS1 locus, between positions 2408 and 2409 of the AAVS1 locus, or a combination thereof.

12. The transgenic mammalian cell of claim 10, wherein the transgenic mammalian cell comprises an attL sequence at a first end of the integrated heterologous nucleic acid and an attR sequence at a second end of the integrated heterologous nucleic acid molecule.

13. The transgenic mammalian cell of claim 10, wherein the heterologous nucleic acid comprises a promoter operably linked to the heterologous gene.

14. The transgenic mammalian cell of claim 10, wherein the heterologous nucleic acid does not comprise a gene encoding an antibiotic resistance marker, an SV40 sequence, or a combination thereof.

15. The transgenic mammalian cell of claim 10, wherein the heterologous gene comprises a virus gene, a reporter gene, or a combination thereof.

16. The transgenic mammalian cell of claim 15, wherein the heterologous gene comprises a virus gene and the mammalian cell line supports the replication of a single cycle infectious virus having a deletion of the virus gene.

17. The transgenic mammalian cell of claim 15, wherein the virus gene comprises a gene from herpes simplex virus-1 (HSV-1), herpes simplex virus-2 (HSV-2), cytomegalovirus, rotavirus, smallpox, poliovirus, rabies virus, reovirus, Japanese encephalitis virus, hemorrhagic fever virus, measles virus, influenza virus, middle-eastern respiratory syndrome coronavirus, dengue virus, Zika virus, SARS-CoV2, or a combination thereof.

18. The transgenic mammalian cell of claim 15, wherein the virus gene comprises an essential gene or a combination of an essential gene and a non-essential gene.

19. The transgenic mammalian cell of claim 15, wherein the virus gene comprises an HSV gene, and the HSV gene comprises glycoprotein B, glycoprotein C, glycoprotein D, glycoprotein E, glycoprotein G, glycoprotein H, glycoprotein I, glycoprotein J, glycoprotein K, glycoprotein L, glycoprotein M, glycoprotein N, UL20, UL45, US9, or a combination thereof or a combination thereof.

20. The transgenic mammalian cell of claim 19, wherein the cell line supports the replication of a single cycle infectious HSV-2 having a genome comprising a deletion of the HSV-2 gD gene or a single cycle infectious HSV-1 having a genome comprising a deletion of the HSV-1 gD gene.

21. The transgenic mammalian cell of claim 10, wherein the mammalian cell comprises 1 to 50 copies of the heterologous nucleic acid integrated in the target locus.

22. A cell line comprising the transgenic mammalian cell of claim 10.

23. A method of producing a transgenic mammalian cell comprising a heterologous nucleic acid stably integrated in a target locus on a chromosome of the transgenic mammalian cell genome, the method comprising:
contacting the genetically modified mammalian cell of claim 1 with
a heterologous nucleic acid comprising a heterologous gene and a recombination sequence comprising an attP sequence from bacteriophage Bxb1, and
an mRNA encoding a bacteriophage Bxb1 integrase and a nuclear localization sequence; and
inserting the heterologous nucleic acid at the target locus in the genetically modified mammalian cell by sequence-specific recombination between the Bxb1 attB sequence in the genetically modified mammalian cell and the attP sequence in the heterologous nucleic acid mediated by the Bxb1 integrase, to produce the transgenic mammalian cell.

24. The method of claim 23, wherein the attP sequence has the sequence of GGTTTGTCTGGTCAAC-CACCGCGGTCTCAGTGGTGTACGGTACAAACC (SEQ ID NO. 3).

25. The method of claim 23, wherein the contacting comprises transfecting the genetically modified mammalian cell with the heterologous nucleic acid and the mRNA.

26. The method of claim 23, wherein the heterologous nucleic acid comprises a promoter and optionally a selectable marker operably linked to the heterologous gene sequence.

27. The method of claim 23, wherein the heterologous nucleic acid further comprises a selectable marker operably linked to the heterologous gene sequence.

28. The method of claim 27, wherein the selectable marker comprises a *Salmonella typhimurium* hisD gene sequence.

29. The method of claim 23, wherein the mammalian cell is a Vero cell and the target locus comprises adeno-associated virus integration site 1 (AAVS1) on chromosome 6 of the Vero cell genome, wherein the heterologous nucleic acid is inserted between positions 1529 and 1530 of the AAVS1 locus, between positions 2155 and 2156 of the AAVS1 locus, between positions 2408 and 2409 of the AAVS1 locus, or a combination thereof.

30. The method of claim 23, wherein the heterologous nucleic acid does not comprise a gene encoding an antibiotic resistance marker, an SV40 sequence, or a combination thereof.

31. The method of claim 23, wherein the transgenic mammalian cell comprises 1 to 50 copies of the heterologous nucleic acid inserted in the target locus.

32. The method of claim 23, wherein the heterologous gene comprises a virus gene, a reporter gene, or a combination thereof.

33. The method of claim 23, wherein the genetically modified mammalian cell is prepared by a process comprising:
providing a complex comprising a guide RNA comprising an oligonucleotide sequence that hybridizes with a target site on the target locus, and a Cas9 endonuclease;
providing a single stranded DNA sequence comprising the Bxb1 attB sequence from *Mycobacterium smegmatis*; and
introducing the complex and the single stranded DNA sequence into the mammalian cell to obtain a mammalian cell comprising the Bxb1 attB sequence inserted in the target locus.

34. A method of propagating a single cycle infectious virus comprising a genome having a deletion of an essential gene, the method comprising:
providing a transgenic mammalian cell of claim 10 comprising at least one copy of the essential gene inserted in a target locus on a chromosome of the mammalian cell genome, wherein the transgenic mammalian cell constitutively expresses a protein encoded by the essential gene;
contacting the transgenic mammalian cell with the single cycle infectious virus; and
complementing the single cycle infectious virus with the protein expressed by the transgenic mammalian cell to propagate the single cycle virus.

35. The method of claim 34 wherein the contacting comprises adding the single cycle infectious virus to the transgenic mammalian cell under conditions that facilitate infection of the transgenic mammalian cell with the single cycle infectious virus.

36. The method of claim 34, wherein the heterologous nucleic acid further comprises hisD as a selection marker, and the method further comprises cultivating the transgenic mammalian cell in a selection medium comprising histidinol for a period of time and under conditions suitable to maximize production of the single cycle infectious virus.

37. The method of any claim 34, wherein the single cycle infectious virus comprises herpes simplex virus-1 (HSV-1), herpes simplex virus-2 (HSV-2), cytomegalovirus, rotavirus, smallpox, poliovirus, rabies virus, reovirus, Japanese encephalitis virus, hemorrhagic fever virus, measles virus, influenza virus, middle-eastern respiratory syndrome coronavirus, Zika virus, SARS-CoV2, or a combination thereof.

38. The method of claim 34, wherein the single cycle infectious virus is a single cycle infectious HSV-1 or a single cycle infectious HSV-2, and wherein the essential gene comprises glycoprotein B, glycoprotein C, glycoprotein D, glycoprotein E, glycoprotein G, glycoprotein H, glycoprotein I, glycoprotein J, glycoprotein K, glycoprotein L, glycoprotein M, glycoprotein N, UL20, UL45, US9, or a combination thereof.

39. A method for detecting and/or quantifying infectious virus in a sample, the method comprising:
providing a transgenic mammalian cell line according to claim 22 comprising transgenic mammalian cells with a heterologous nucleic acid stably integrated in a target locus on a chromosome of the genome of the mammalian cells, wherein the heterologous nucleic acid comprises a virus promoter operably linked to a reporter gene;
contacting the transgenic mammalian cells with the sample, wherein infectious virus present in the sample transactivates the virus promoter and induces expression of the reporter gene in the transgenic mammalian cells; and
quantifying the number of mammalian cells expressing protein encoded by the reporter gene to quantify the infectious virus.

40. The method of claim 39, wherein the contacting comprises infecting the transgenic mammalian cells with virus present in the sample.

41. The cell based reporter assay of claim 39, further comprising detecting expression of the reporter gene in the transgenic mammalian cells.

42. The cell based reporter assay of claim 39, wherein the reporter gene encodes a fluorescent protein comprising luciferase, nano-Luc, beta-lactamase, alkaline phosphatase, green fluorescent protein, Venus, monomeric Infrared Fluorescent Protein (mIFP), Long Stokes Shift monomeric Orange (LssmOrange), Red Fluorescent Protein (RFP), Tag Red Fluorescent Protein 657 (TagRFP657), monomeric Orange2 (mOrange2), monomeric Apple (mApple), Sapphire, monomeric Tag Blue Fluorescent Protein (mTagBFP2), tdTomato, monomeric Cherry (mCherry), Yellow Fluorescent Protein (YFP), Enhanced Yellow Fluorescent Protein (EYFP), monomeric Cerulean3 (mCerulean3), Green Fluorescent Protein (GFP), Enhanced Green Fluorescent Protein (EGFP), or a combination thereof.

43. The method of claim 39, wherein the sample is a biological sample from a subject or a sample taken from a batch of bulk virus.

44. The method of claim 43, wherein the biological sample comprises serum, saliva, plasma, whole blood, nasopharyngeal swab, urine, stool, respiratory fluid, cerebrospinal fluid, or a combination thereof.

* * * * *